(12) United States Patent
Booth et al.

(10) Patent No.: US 7,232,837 B2
(45) Date of Patent: Jun. 19, 2007

(54) STEREOISOMERS WITH HIGH AFFINITY FOR ADRENERGIC RECEPTORS

(75) Inventors: Anthony Booth, Chester, NJ (US); James L. Caffrey, Burelson, TX (US)

(73) Assignee: McNeil-PPC, Inc., New Brunswick, NJ (US)

( * ) Notice: Subject to any disclaimer, the term of this patent is extended or adjusted under 35 U.S.C. 154(b) by 0 days.

(21) Appl. No.: 10/681,915

(22) Filed: Oct. 9, 2003

(65) Prior Publication Data

US 2004/0073043 A1   Apr. 15, 2004

Related U.S. Application Data

(60) Division of application No. 10/106,513, filed on Mar. 25, 2002, now Pat. No. 6,664,424, which is a continuation of application No. 09/342,704, filed on Jun. 29, 1999, now abandoned.

(51) Int. Cl.
*A61K 31/44* (2006.01)
*C07D 211/04* (2006.01)

(52) U.S. Cl. ...................... 514/345; 514/345; 546/343

(58) Field of Classification Search ................ 546/343; 514/345
See application file for complete search history.

(56) References Cited

U.S. PATENT DOCUMENTS

| | | | |
|---|---|---|---|
| 3,644,353 A | 2/1972 | Lunts et al. | |
| 3,885,047 A | 5/1975 | Seidehamel et al. | |
| 3,985,897 A | 10/1976 | Seidehamel et al. | |
| 4,695,580 A | 9/1987 | Ohashi et al. | |
| 4,727,078 A * | 2/1988 | Terao et al. | 514/277 |
| 4,853,381 A | 8/1989 | Finch et al. | |
| 4,876,436 A | 10/1989 | Ide et al. | |
| 5,248,695 A | 9/1993 | Resemann et al. | |
| 5,292,753 A | 3/1994 | Resemann et al. | |
| 5,362,755 A | 11/1994 | Barberich et al. | |
| 5,380,729 A | 1/1995 | DeHaven-Hudkins et al. | |
| 5,395,957 A | 3/1995 | Resemann et al. | |
| 5,399,765 A | 3/1995 | Gao et al. | |
| 5,442,118 A | 8/1995 | Gao et al. | |

(Continued)

FOREIGN PATENT DOCUMENTS

BE           756973Q       2/1971

(Continued)

OTHER PUBLICATIONS

Corey, E. J. and Christopher J. Helal, "Asymmetric Synthesis of (S)-carbinoxamine, New Aspects of Oxazaborolidine-catalyzed Enantioselective Carbonyl Reduction," Tetrahedron Letters (1996), 37 (32), pp. 5675-5678.*

(Continued)

*Primary Examiner*—Kamal A. Saeed
*Assistant Examiner*—Janet L. Coppins
(74) *Attorney, Agent, or Firm*—Evan J. Federman

(57) ABSTRACT

The present invention provides stereoscopically-pure diastereomers of Formula I:

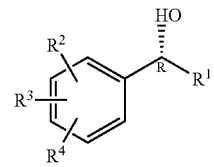

I

In a preferred embodiment, the stereoisomers of the present invention are of Formula II, depicted below:

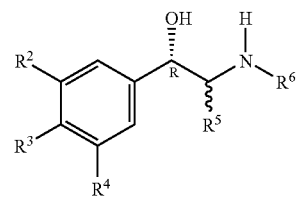

II $R^2$, $R^3$ and $R^4$ are independently H, OH, $OCH_3$, $CH_2OH$, $NHCONH_2$, $NH_2$, halogen or $CF_3$, and $R^1$ is pyridine, or an amine which may be substituted with hydrogen, lower alkyl, lower alkylenearyl, lower alkylenephenyl, lower alkylenehydroxyphenyl, lower alkyleneamine, lower alkyleneaminoaryl, lower alkylaminohydroxyphenyl, or a similar functional group. $R^5$ is hydrogen, hydroxyl or methyl; $R^6$ is hydrogen, lower alkyl, lower alkylenaryl, lower alkylenephenyl, lower alkylenehydroxyphenyl, lower alkyleneamine, lower alkyleneaminoaryl, lower alkylaminohydroxyphenyl, and the like. For both Formula I and Formual II, the first carbon on the side chain progressing from the ring is preferably in the R-configuration. The second carbon atom on the side chain of Formula II, which is attached to $R^5$, may or may not be a chiral center. However, when the second carbon atom is a chiral center, it is preferably in the S-configuration. The present invention contemplates each stereoisomer of Formula I and II in substantially-pure form.

The present invention also provides methods of relieving nasal, sinus and bronchial congestion and of treating attention deficit hyperactivity disorder and obesity. The present stereoisomers may also be used to induce pupil dilation. These methods include administering to a mammal a composition containing a therapeutically effective amount of a stereoscopically-pure stereoisomer of Formula I or II with a pharmaceutically acceptable excipient.

1 Claim, 3 Drawing Sheets

U.S. PATENT DOCUMENTS

| | | |
|---|---|---|
| 5,545,745 A | 8/1996 | Gao et al. |
| 5,547,994 A | 8/1996 | Barberich et al. |
| 5,648,386 A | 7/1997 | Resemann et al. |
| 5,708,036 A | 1/1998 | Pesterfield, Jr. |

FOREIGN PATENT DOCUMENTS

| | | |
|---|---|---|
| BE | 768120Q | 6/1971 |
| BE | 786261Q | 7/1971 |
| CA | 2065051 | 10/1997 |
| DE | 2400533 | 1/1973 |
| EP | 390762 A | 3/1989 |
| EP | 455155 A | 5/1990 |
| EP | 460924 A | 3/1991 |
| EP | 0422889 | 4/1991 |
| JP | 4151935 | 5/1978 |
| JP | 0132935 | 12/1983 |
| JP | 1007238 | 6/1984 |
| JP | 1085197 | 10/1984 |
| JP | 2228298 | 3/1986 |
| NL | 7303612 | 9/1973 |
| NL | 7308193 | 12/1973 |
| WO | WO 9109596 | 1/1990 |
| WO | WO9318007 | 3/1992 |
| WO | WO9508529 | 9/1993 |
| WO | WO 9532178 | 1/1995 |
| WO | WO9730023 | 2/1996 |
| WO | WO 9726871 | 8/1996 |

OTHER PUBLICATIONS

CAPLUS Accession No. 1990:98344, abstract of "Synthesis of some optically active alpha-pyridylcarbinols from the CD of their in situ complexes with Mo2(OAc)4," (1989), Berova et al, vol. 62(2B), pp. 411-422.*

* cited by examiner

Figure 1:
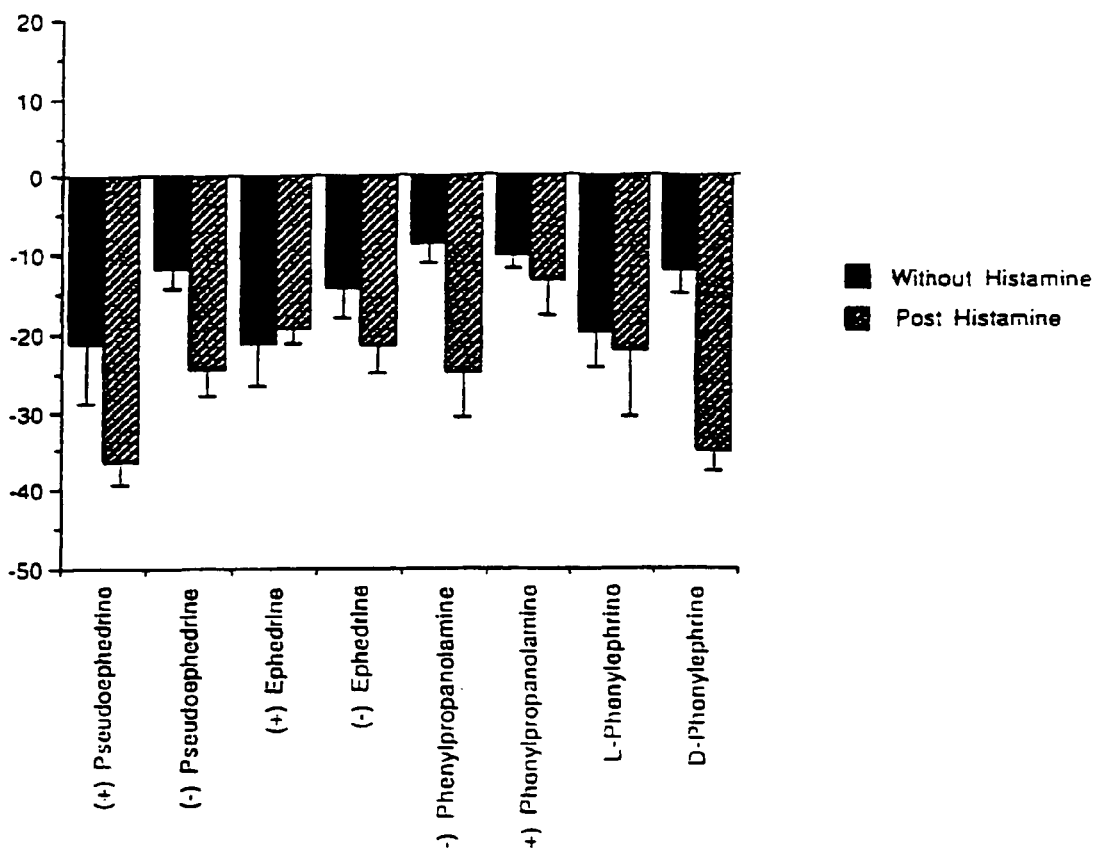

Figure 1. Nasal airway pressure responses to decongestant enantiomeres with and without a histamine challenge

STEREOISOMERS WITH HIGH AFFINITY FOR ADRENERGIC RECEPTORS

This application is a divisional application of U.S. Ser. No. 10/106,513, filed Mar. 25, 2002 now U.S. Pat. No. 6,664,424, which is a continuation application of U.S. Ser. No. 09/342,704, filed on Jun. 29,1999 now abandoned.

FIELD OF THE INVENTION

The present application provides stereoisomers with high affinity for adrenergic receptors which may be used in pharmaceutical compositions and as therapeutic agents in a variety of methods. The present stereoisomers can also be used to identify other compounds that bind to adrenergic receptors, for example, by way of competitive binding studies. The present stereoisomers can act as decongestants, bronchodilators, physiological antagonists of histamine, mydriatic agents, appetite suppressants, and be used for treating conditions typically treated with sympathomimetic drugs. These new stereoisomers are described by Formula I or Formula II.

Formula I embraces the stereoisomers depicted below:

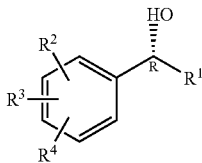

I wherein $R^2$, $R^3$ and $R^4$ are independently H, OH, $OCH_3$, $CH_2OH$, $NHCONH_2$, $NH_2$, halogen or $CF_3$, and $R^1$ is pyridine, or an amine which may be substituted with hydrogen, lower alkyl, lower alkylenearyl, lower alkylenephenyl, lower alkylenehydroxyphenyl, lower alkyleneamine, lower alkyleneaminoaryl, lower alkylaminohydroxyphenyl, or a similar functional group. According to the present invention, the first carbon on the side chain progressing from the ring is preferably in the R-configuration.

In a preferred embodiment, the stereoisomers of the present invention are of Formula II, depicted below:

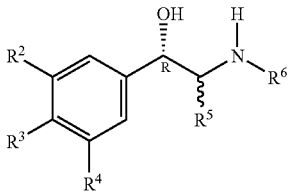

II wherein $R^5$ is hydrogen, hydroxyl or methyl; $R^6$ is hydrogen, lower alkyl, lower alkylenearyl, lower alkylenephenyl, lower alkylenehydroxyphenyl, lower alkyleneamine, lower alkyleneaminoaryl, lower alkylaminohydroxyphenyl, and the like. As for Formula I, the first chiral carbon atom on the side chain progressing from the ring in Formula II is preferably in the R-configuration. The second carbon atom on the side chain of Formula II may or may not be a chiral center, however, when the second carbon atom is a chiral center it is preferably in the S-configuration. The present invention contemplates each stereoisomer of Formula I and Formula II in substantially-pure form.

In an even more preferred embodiment, $R^5$ is hydroxy or methyl in the S-configuration.

In some embodiments, the compositions of the present invention preferably do not include (−)-phenylpropanolamine, (−)phenylephrine, (−)-ephedrine, adrenaline, albuterol, ambuterol, carbuterol, clenbuterol, fenoterol, isoetharine, isoprenaline, metaproterenol, orciprenaline, pirbuterol, rimiterol, saimeterol, terbutaline, tolobuterol, salmeterol, or salbutamol. According to the present invention, the Formula I and Formula II stereoisomers can act as decongestants, bronchodilators, physiological antagonists of histamine, mydriatic agents, appetite suppressants, and be used for treating conditions typically treated with sympathomimetic drugs. However, also according to the present invention, the stereoisomers of Formula I have particular utility for binding to $β_2$ adrenergic receptors and for acting as bronchodilators.

BACKGROUND OF THE INVENTION

The present stereoisomers are structurally related to some sympathomimetic drugs. Generally, sympathomimetic amines act by binding to α- and β-adrenergic receptors. Such receptor binding can result in vascular constriction, reduced blood flow and/or reduced secretion of fluids into the surrounding tissues, which can decrease the amount of mucous secreted into nasal passages. Sympathomimetic drugs are thus used to treat nasal congestion, allergies and colds. In addition, sympathomimetic amines may affect the cardiovascular, urinary, central nervous and endocrine systems. Johnson et al., 13 Pharmacotherapy 1105 (1993). Sympathomimetic drugs can influence the smooth muscles and the activity of the central nervous system. Thus, sympathomimetic amines are also used as bronchodilators, appetite suppressants and mydriatic agents.

According to the present invention, stereoisomers with particular structural configurations interact more selectively with the receptors involved in sympathomimetic action than do other types of stereoisomers. Compounds with more than one chiral center that differ in the configuration of some but not all of the chiral centers are called diastereomers. Compounds that have the same composition but are mirror images of each other are called enantiomers. A chiral center is an asymmetric carbon atom which can exist in two different, mirror-image configurations. Compounds with such chiral centers have the ability to rotate the plane of plane-polarized light. The prefixes d and l, or (+) and (−) identify the direction in which a stereoisomer rotates light. The d or (+)-stereoisomer is dextrorotatory. In contrast, the l or (−)-stereoisomer is levorotatory. A mixture of (+) and (−)-enantiomers is called a racemic mixture.

An alternative classification system for stereoisomers exists where prefixes (S) and (R) are used, based on the structural configuration of the chiral center, rather than on the optical activity of the compound.

For example, (+)-pseudoephedrine is known to be a sympathomimetic amine which binds to α-adrenergic receptors. The structures of (+)-pseudoephedrine and (−)-pseudoephedrine are provided below.

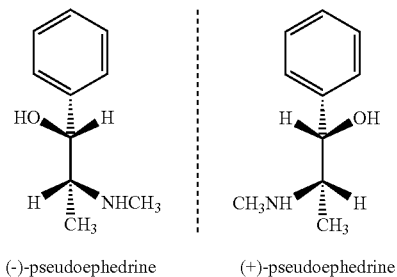

(−)-pseudoephedrine      (+)-pseudoephedrine (+)-Pseudoephedrine is a known decongestant sold under the tradename Sudafed®. However, (+)-pseudoephedrine has undesirable side effects, including central nervous system stimulation, lightheadedness, nervousness, anxiety, paranoia, heart arrhythmia, atrial fibrillations and premature ventricular contractions. 95 AMERICAN HOSPITAL FORMULATORY SERVICE 847–48. Moreover, (+)-pseudoephedrine unfortunately can be converted into the psychoactive drug, methamphetamine, by simply converting the hydroxyl, which is in the S-configuration, to the hydrogen found in methamphetamine. Hence, a need exists for a molecule which binds to an adrenergic receptor, has the beneficial decongestant activities of (+)-pseudoephedrine, and which reduces not only its adverse side effects, but its methamphetamine-conversion problem.

(−)-Ephedrine and the racemic mixture of (−)- and (+)-ephedrine also bind adrenergic receptors and have been used for bronchodilation. (−)-Ephedrine and the racemic mixture of (−) and (+)-ephedrine relax smooth muscle, stimulate metabolism, stimulate the central nervous system, but can have significant cardiovascular effects. 95 AMERICAN HOSPITAL FORMULATORY SERVICE 815. Accordingly, a need exists for molecules which bind adrenergic receptors, without the undesirable side effects of (−)-ephedrine and the racemic mixture of (−)-ephedrine and (+)-ephedrine.

Similarly, the racemic mixture of (+)- and (−)-phenylpropanolamine, is known to bind adrenergic receptors, and has been used as a decongestant or an anoretic. However, the racemic mixture has undesirable side effects—it may be contraindicated in patients having glaucoma and is known to stimulate the central nervous system. 95 AMERICAN HOSPITAL FORMULATORY SERVICE 846. Hence, a need exists for a composition having the beneficial activities of (+)- and (−)-phenylpropanolamine, without their undesirable side effects.

SUMMARY OF THE INVENTION

The present invention is directed to a stereoscopically-pure stereoisomer of Formula I or Formula II, and a pharmaceutically acceptable carrier, with the proviso that the stereoisomer is not (−)-phenylpropanolamine, (−)-phenylephrine or (−) ephedrine. The present stereoisomers bind to adrenergic receptors with high affinity. According to the present invention, compositions containing a stereoisomer of Formula I or Formula II have a variety of uses. For example, when provided in a therapeutically effective dosage, the stereoisomers of the present invention may be used to treat nasal congestion, bronchial congestion, asthma, attention deficit hyperactivity disorder (ADHD), inflammation caused by histamine, and other conditions treated with sympathomimetic drugs. The present stereoisomers may also be used to dilate the pupil and to suppress the appetite.

The present Formula I stereoisomers bind to adrenergic receptors, preferably $\beta_2$ adrenergic receptors, with high affinity. When used for some purposes, the stereoisomers of Formula I and II may not include adrenaline, albuterol, ambuterol, carbuterol, clenbuterol, fenoterol, isoetharine, isoprenaline, metaproterenol, orciprenaline, pirbuterol, rimiterol, salmeterol, terbutaline, tolobuterol, salmeterol, or salbutamol.

The present invention is also directed to a method of identifying compounds that bind to adrenergic receptors which includes preparing a mixture of a test compound and a stereoscopically-pure stereoisomer of Formula I or II, contacting the mixture to an adrenergic receptor and detecting whether the test compound binds to the adrenergic receptor. According to the present invention, test compounds that can effectively compete with the present stereoisomers for the binding sites in adrenergic receptors will also bind adrenergic receptors with high affinity.

The present invention is also directed to a method of relieving nasal and/or bronchial congestion which includes administering a therapeutically effective amount of a stereoscopically-pure stereoisomer of a compound of Formula I or II. For this method the stereoisomer is preferably not (−)-phenylpropanolamine, (−)-phenylephrine, (−)-ephedrine, adrenaline, albuterol, ambuterol, carbuterol, clenbuterol, fenoterol, isoetharine, isoprenaline, metaproterenol, orciprenaline, pirbuterol, rimiterol, salmeterol, terbutaline, tolobuterol, salmeterol, or salbutamol. In this embodiment, a therapeutically effective amount of the stereoisomer is a dosage suitable for treating nasal and/or bronchial congestion.

The present invention is also directed to a method of antagonizing the physiological effects of histamine which includes administering a therapeutically effective amount of a stereoscopically-pure stereoisomer of a compound of Formula I or II. For this purpose, the stereoisomer is preferably not (−)-phenylpropanolamine, (−)-phenylephrine, (−)-ephedrine, adrenaline, albuterol, ambuterol, carbuterol, clenbuterol, fenoterol, isoetharine, isoprenaline, metaproterenol, orciprenaline, pirbuterol, rimiterol, salmeterol, terbutaline, tolobuterol, salmeterol, or salbutamol. In this embodiment, a therapeutically effective amount of the stereoisomer is a dosage suitable for relieving the physiological effects of histamine. Such physiological effects include, for example, nasal congestion, inflammation and other allergic responses.

The present invention is further directed to a method of dilating the pupil which includes administering a therapeutically effective amount of a stereoscopically-pure stereoisomer of Formula I or II, to a mammal. For this method the stereoisomer is preferably not (−)-phenylpropanolamine, (−)-phenylephrine, or (−)-ephedrine. The stereoisomer is preferably administered topically. In this embodiment, a therapeutically effective amount of the stereoisomer is a dosage suitable for dilating the eye pupil.

The present invention is also directed to a method of treating conditions typically treated with sympathomimetic drugs, which includes administering a therapeutically effective amount of a stereoscopically-pure stereoisomer of Formula I or II to a mammal. In some embodiments, the present stereoisomer for this method is not (−)-phenylpropanolamine, (−)-phenylephrine, (−)-ephedrine, adrenaline, albuterol, ambuterol, carbuterol, clenbuterol, fenoterol, isoetharine, isoprenaline, metaproterenol, orciprenaline, pirbuterol, rimiterol, salmeterol, terbutaline, tolobuterol, salmeterol, or salbutamol. In this embodiment, a therapeutically effective amount of the stereoisomer is a dosage suitable for treating the condition typically treated with a sympathomimetic drug.

BRIEF DESCRIPTIONS OF THE DRAWINGS

FIG. 1 depicts the percent change in nasal airway passage pressure in rats treated with (+)-pseudoephedrine, (+)-ephedrine, (−)-ephedrine, (−)-phenylpropanolamine, (+)-phenylpropanolamine, (−)-phenylephrine and (+)-phenylephrine, alone (solid bar) or after congestion was induced by administering histamine (stippled bar).

Figure 2:
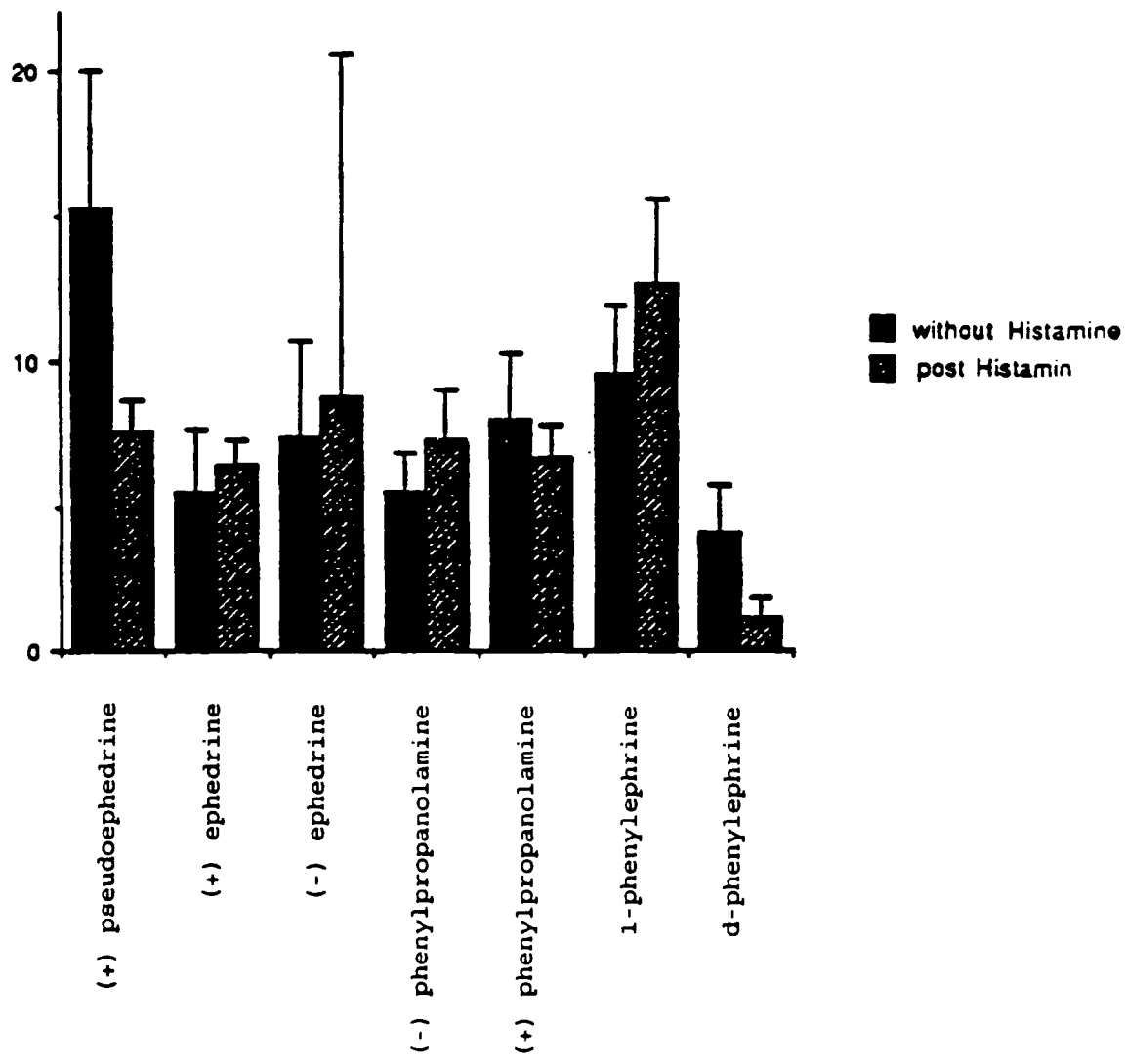

FIG. 2 depicts the percent change in mean arterial blood pressure in rats treated with a "75% dose" of (+)-pseudoephedrine, (+)-ephedrine, (−)-ephedrine, (−)-phenylpropanolamine, (+)-phenylpropanolamine, (−)-phenylephrine and (+)-phenylephrine. The "75% dose" of these drugs is 75% of the dose needed to raise the mean arterial pressure by 10%. The solid bar shows the effect of the drug alone, whereas the stippled bar shows the effect of the drug on blood pressure after congestion was induced by administering histamine.

Figure 3:
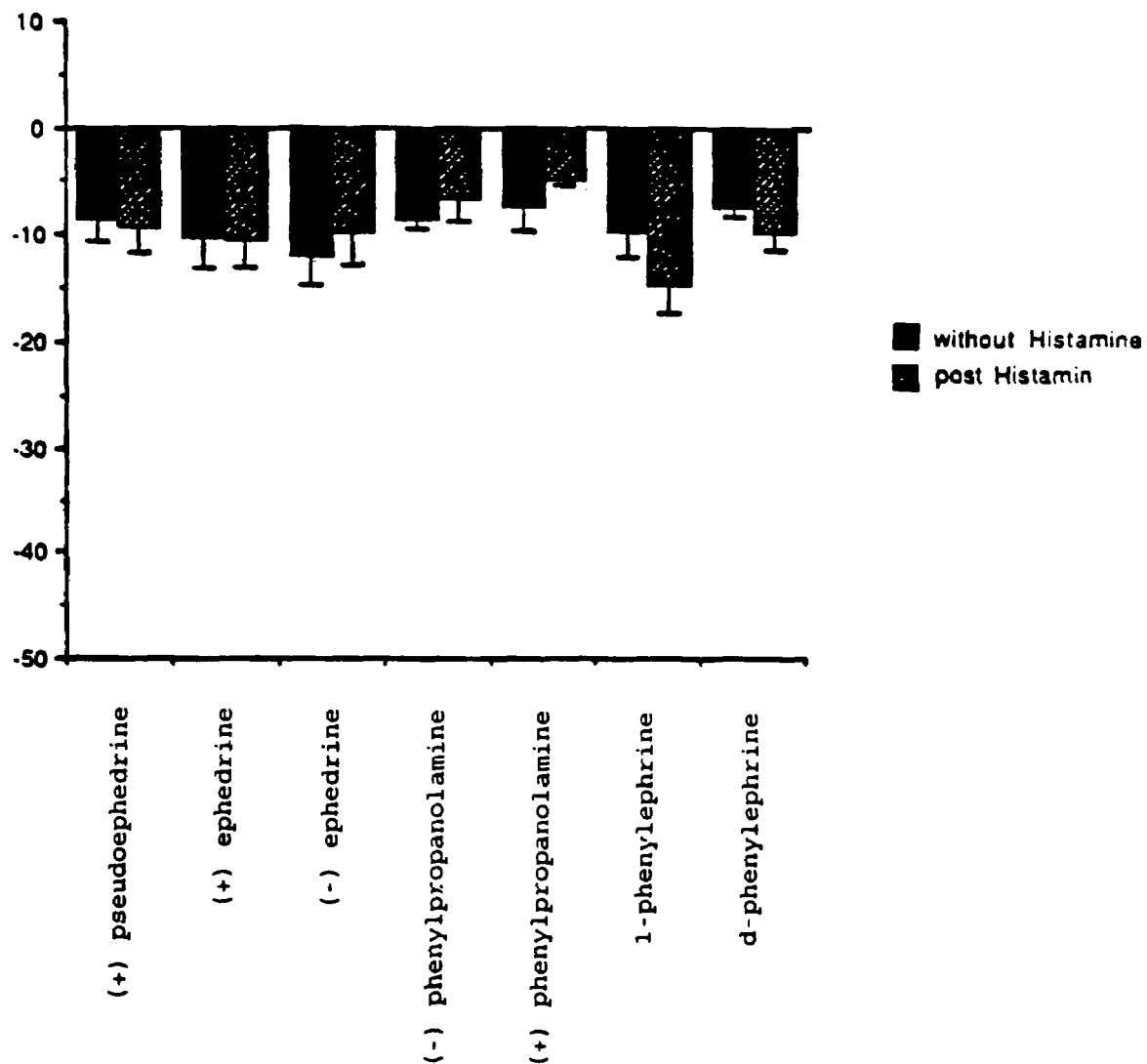

FIG. 3 depicts the percent change in nasal airway passage pressure in rats treated with a "75% dose" of (+)-pseudoephedrine, (+)-ephedrine, (−)-ephedrine, (−)-phenylpropanolamine, (+)-phenylpropanolamine, (−)-phenylephrine and (+) phenylephrine. The "75% dose" of these drugs is 75% of the dose needed to raise the mean arterial pressure by 10%. The solid bar shows the effect of the drug alone, whereas the stippled bar shows the effect of the drug on airway pressure after congestion was induced by administering histamine.

DETAILED DESCRIPTION OF THE INVENTION

Formula I embraces the stereoisomers depicted below:

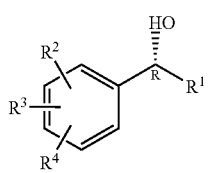

I wherein $R^2$, $R^3$ and $R^4$ are independently H, OH, $OCH_3$, $CH_2OH$, $NHCONH_2$, $NH_2$, halogen or $CF_3$, and $R^1$ is pyridine, or an amine which may be substituted with hydrogen, lower alkyl, lower alkylenearyl, lower alkylenephenyl, lower alkylenehydroxyphenyl, lower alkyleneamine, lower alkyleneaminoaryl, lower alkylaminohydroxyphenyl, or a similar functional group. According to the present invention, the first carbon on the side chain progressing from the ring is preferably in the R-configuration. This means that the carbon attached to the OH is in the (R)-configuration.

In a preferred embodiment, the stereoisomers of the present invention are of Formula II, depicted below:

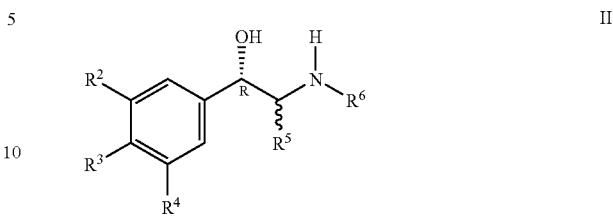

II wherein $R^5$ is hydrogen, hydroxyl or methyl; $R^6$ is hydrogen, lower alkyl, lower alkylenaryl, lower alkylenephenyl, lower alkylenehydroxyphenyl, lower alkyleneamine, lower alkyleneaminoaryl, lower alkylaminohydroxyphenyl, and the like. As for Formula I, the first chiral carbon atom on the side chain progressing from the ring in Formula II is preferably in the R-configuration The second carbon atom on the side chain of Formula II, which is attached to $R^5$, may or may not be a chiral center. However, when the second carbon atom is a chiral center, it is preferably in the S-configuration. The present invention contemplates each stereoisomer of Formula I and II in substantially-pure form.

In an even more preferred embodiment, $R^5$ is hydroxy or methyl in the S-configuration.

According to the present invention, lower alkyl means a branched or non-branched hydrocarbon chain having one to six carbon atoms. Thus, lower alkyl groups of the present invention include methyl, ethyl, propyl, isopropyl, butyl, isobutyl, tert-butyl, pentyl, isopentyl, hexyl and related groups.

The present invention contemplates a number of uses for the present stereoisomers. For example, according to the present invention, the Formula I and Formula II stereoisomers can act as decongestants, bronchodilators, physiological antagonists of histamine, mydriatic agents, appetite suppressants, and be used for treating conditions typically treated with sympathomimetic drugs. However, also according to the present invention, the stereoisomers of Formula I have particular utility for binding to $\beta_2$ adrenergic receptors and for acting as bronchodilators. In some embodiments, the compositions for these uses preferably do not include (−)-phenylpropanolamine, (−)-phenylephrine, (−)-ephedrine, adrenaline, albuterol, ambuterol, carbuterol, clenbuterol, fenoterol, isoetharine, isoprenaline, metaproterenol, orciprenaline, pirbuterol, rimiterol, salmeterol, terbutaline, tolobuterol, salmeterol, or salbutamol.

In one embodiment, the present stereoisomers may be used to isolate other compounds which bind to adrenergic receptors. The present compounds may also be used for treating colds, nasal congestion, bronchial congestion or constriction, histamine-related inflammations, allergies, obesity, and attention deficit hyperactivity disorder. According to the present invention, the stereoisomers of Formula II are particularly useful for binding to $\beta_2$ adrenergic receptors and for providing bronchodilation. In another embodiment, the present stereoisomers may be used for dilating the pupil. In general, the present invention contemplates using these stereoisomers for any condition typically treated with a sympathomimetic drug. The present invention further contemplates pharmaceutical compositions of the present stereoscopically-pure stereoisomers which include a pharmaceutically acceptable carrier.

As used herein, the term "stereoscopically pure stereoisomer" of Formula I or Formula II means that the composition contains at least 90% of such a stereoisomer, and 10% or less of another stereoisomer. In a more preferred embodiment, such a "stereoscopically-pure stereoisomer" means that the composition contains at least 95% of that stereoisomer and 5% or less of another stereoisomer. Still more preferred is an embodiment wherein the pharmaceutical composition contains 99% or more of the preferred stereoisomer and 1% or less of another stereoisomer.

Similarly, as used herein, the term "substantially free" of another stereoisomer means that the composition contains at least 90% of a stereoisomer of Formula I, and 10% or less of another stereoisomer or stereoisomer. In a more preferred embodiment, "substantially free" of another stereoisomer means that the composition contains at least 95% of the stereoisomer of Formula I and 5% or less of another stereoisomer. Still more preferred is an embodiment wherein the pharmaceutical composition contains 99% or more of the present stereoisomers and 1% or less of another stereoisomer.

According to the present invention, the stereoscopically pure stereoisomers of the present invention bind adrenergic receptors with greater affinity and selectivity than other compounds. For example, the present compounds competitively inhibit binding to adrenergic receptors by known adrenergic receptor ligands. Competitive inhibition procedures can thus be used to evaluate the affinity of the present stereoisomers for adrenergic receptors. Similarly, because the present stereoisomers bind adrenergic receptors with high affinity, competitive inhibition studies employing the present stereoisomers can be used to identify new compounds which also bind to adrenergic receptors.

One of skill in the art can readily perform competitive inhibition studies and use those studies for evaluating the affinity of a test compound for a receptor. For example, competitive inhibition studies are often performed by labeling a known adrenergic receptor ligand, measuring the amount of labeled ligand that binds to adrenergic receptors and comparing that amount to the amount of labeled ligand remaining bound when a test compound is present. If less labeled ligand remains bound to the adrenergic receptor when the test compound is present, the test compound has inhibited ligand binding. This means that the test compound also binds to the adrenergic receptor. The apparent association constant ($K_i$) of the test compound and the concentration at which a test compound inhibits fifty percent of ligand binding ($IC_{50}$) are parameters indicating the effectiveness, or affinity, of binding by the test compound. The lower the $K_i$ and the $IC_{50}$, the greater the affinity of the test compound for the adrenergic receptor.

Several types of adrenergic receptors are known. The present stereoisomers bind to all types of adrenergic receptors, including, for example, $\alpha_1$, $\alpha_2$ and $\beta_2$ adrenergic receptors. According to the present invention, the present stereoisomers preferably have a $K_i$ value of less than about 50 μM and an $IC_{50}$ of less than about 120 μM for $\alpha_1$ adrenergic receptors, when labeled prazocin is used as the competitive ligand. The present stereoisomers preferably have a $K_i$ value of less than about 1 μM and an $IC_{50}$ which is also less than about 1 μM for $\alpha_2$ adrenergic receptors, when labeled iodoclonidine is used as the competitive ligand. The present stereoisomers also preferably have a $K_i$ value of less than about 25 μM and an $IC_{50}$ of less than about 60 μM for $\beta_2$ adrenergic receptors, when labeled iodocyanopindolol is used as the competitive ligand. According to the present invention the stereoisomers of Formula II are particularly effective at binding $\beta_2$ adrenergic receptors.

The stereoisomers of this invention may be prepared by known procedures. Methods for separating stereoisomers from a racemic mixture are well-known to the skilled artisan.

The present invention also provides pharmaceutically acceptable salts of the present stereoisomers. For example, the present stereoisomers can be provided as a hydrochloride, bitartrate, tannate, sulfate, stearate, citrate or other pharmaceutically acceptable salts. Methods of making such pharmaceutical salts are readily available to one of ordinary skill in the art.

As used herein, "pharmaceutically acceptable carrier" includes any and all solvents, dispersion media, coatings, isotonic and absorption delaying agents, sweeteners and the like. The pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and adsorbents that may be needed in order to prepare a particular therapeutic composition. The use of such media and agents for pharmaceutical active substances is well known in the art. Except insofar as any conventional media or agent is incompatible with the active ingredient, its use in the therapeutic compositions is contemplated.

The present compounds have little or no interaction with other drugs. Due to the lack of such drug interaction, supplementary active ingredients, such as additional antihistamines and decongestants, can be incorporated into the present compositions. The amount of the added antihistamine or decongestant present in the pharmaceutical composition will depend upon the particular drug used. Typical antihistamines include: diphenhydramine; chlorpheniramine; astemizole; terfenadine; terfenadine carboxylate; brompheniramine; triprolidine; acrivastine; and loratadine.

The present invention contemplates a method of relieving nasal, sinus and/or bronchial congestion which comprises administering a therapeutically effective amount of a stereoscopically-pure enantiomer of a compound of Formula I and Formula II. The present invention further contemplates a method of counteracting the physiological effects of histamine which comprises administering a therapeutically effective amount of a stereoscopically-pure enantiomer of a compound of Formula I and Formula II. The stereoisomers of Formula II are particularly effective for relieving bronchial congestion and for providing bronchial dilation. Thus, the present stereoisomers may be used in a method for treating asthma, bronchitis, pneumonia and other conditions where bronchodilation may be helpful.

According to the present invention, the present stereoisomers are surprisingly more effect as decongestants and as physiological antagonists of histamine than are compounds of another configuration. As a physiological antagonist of histamine, the present stereoisomers counteract the physiological effects of histamine. Histamine can cause nasal congestion, bronchial congestion, inflammation and the like. This invention contemplates the present stereoisomers to counteract all of these histamine-related physiological responses.

The present invention further contemplates a method of dilating the pupil which comprises administering a therapeutically effective amount of a stereoscopically pure enantiomer of a compound of Formula I or II to the eye. Methods of treating obesity and attention deficit hyperactivity disorder are also contemplated by the present invention.

According to the present invention, a therapeutically effective amount of a stereoisomer of the present invention is an amount sufficient to relieve the symptoms of a condition which can be treated by a sympathomimetic drug. In one embodiment, an amount sufficient to reduce the symptoms of a condition which can be treated by a sympathomimetic drug is an amount of stereoisomer sufficient to bind or activate an adrenergic receptor, for example, an α- or a β-adrenergic receptor. When the condition is nasal congestion the therapeutically effective amount is the amount needed to reduce nasal congestion. When bronchial congestion is the condition, the therapeutically effective amount is the amount needed to reduce bronchial congestion, or to provide bronchodilation. When a histamine-related condition like inflammation and/or an allergic reaction is the condition, the therapeutically effective amount is the amount needed to counteract the physiological effects of histamine. When eye pupil dilation is the desired, such a therapeutically effective amount of stereoisomer is an amount sufficient to dilate the pupil. Preferably, such a pharmaceutically effective amount also produces less side effects than are observed upon administration of an stereoisomer of another configuration, or a racemic mixture of compounds. The skilled artisan can readily determine the necessary therapeutically effective amounts for treating these conditions, particularly in light of the teachings provided herein.

The pharmaceutical compositions of the present invention contain a stereoisomer in a therapeutically effective amount that is sufficient to provide decongestion, bronchodilation, treat inflammation, produce a mydriatic response or provide appetite suppression while having less side effects than would similar doses of a stereoisomer of another configuration or the racemic mixture of compounds. Such a therapeutically effective amount would be about 0.1 micrograms (μg) to about 10 milligrams (mg) per kg of body weight per day, and preferably of about 1.0 μg to about 1 mg per kg of body weight per day. More preferably the dosage can range from about 10 μg to about 500 μg per kg of body weight per day. Dosages can be readily determined by one of ordinary skill in the art and can be readily formulated into the subject pharmaceutical compositions.

The subject stereoisomers may be administered by any convenient route. For example, the stereoisomer may be inhaled, ingested, topically applied or parenterally injected. The subject stereoisomers may be incorporated into a cream, solution or suspension for topical administration. In one embodiment, the present stereoisomers are preferably inhaled or administered orally or topically. The skilled artisan can readily determine the route for a specific use.

The following examples further illustrate the invention.

EXAMPLE 1

Compounds Tested

Many of the compounds of the present invention have two asymmetric carbon centers on the side chain leading from the ring. According to the present invention, the first asymmetric carbon center has an R configuration and the second asymmetric carbon center may have an S configuration. Compounds tested for binding affinity to adrenergic receptors are shown below.

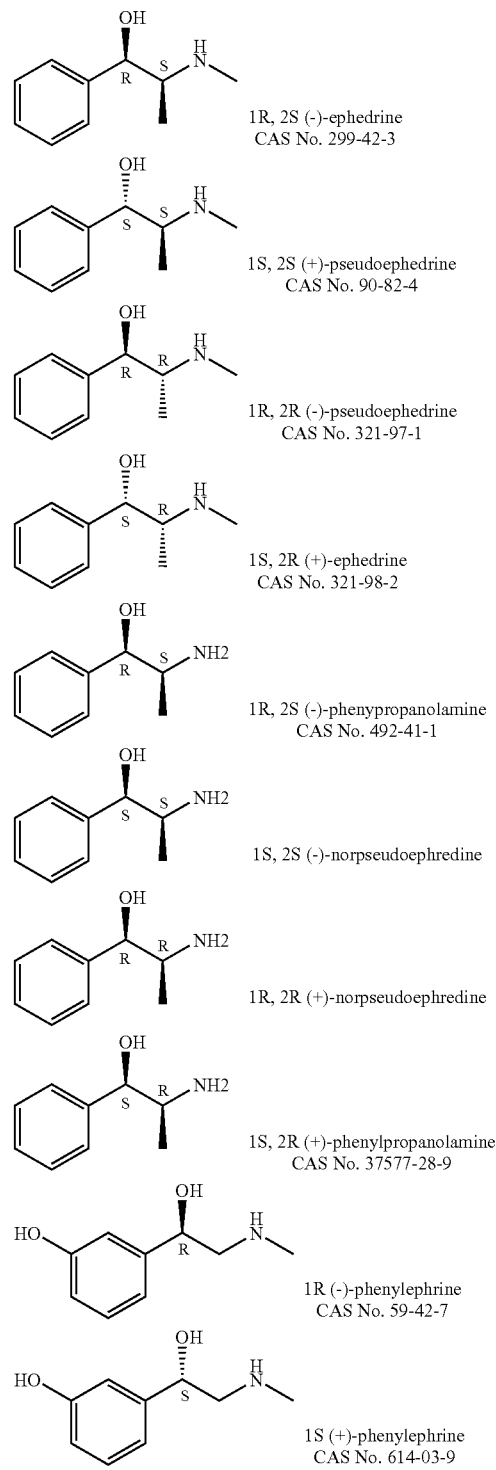

EXAMPLE 2

α-Adrenergic and β-Adrenergic Receptor Binding Studies

Many physiological processes are mediated by the binding of chemical compounds to $\alpha_1$, $\alpha_2$ and $\beta_2$ receptors. For example, many compounds which reduce nasal congestion bind to $\alpha_1$ and $\alpha_2$ receptors and some reduce bronchial congestion by binding to $\beta$ receptors. Accordingly, a compound that binds to $\alpha_1$, $\alpha_2$ and/or $\beta_2$ receptors may be an effective nasal or bronchial decongestant.

More specifically, $\alpha_2$ adrenergic receptors, concentrated on precapillary arterioles in the nasal mucosa, induce arteriolar vasoconstriction when activated by a sympathomimetic compound. Such vasoconstriction decreases blood flow through those vessels and reduces excess extracellular fluid associated with nasal congestion and a runny nose. On the other hand, $\alpha_1$ adrenergic receptors are concentrated on postcapillary venules in the nasal mucosa Binding to $\alpha_1$ receptors induces venoconstriction, which also reduces nasal congestion.

Compounds that bind to $\beta_2$ receptors may also help relieve the symptoms of bronchial congestion because $\beta_2$ receptor binding is related to increased bronchodilation and reduced airway resistance.

The binding of the present compounds to $\alpha_1$, $\alpha_2$ and $\beta_2$ receptors was compared to that of known sympathomimetic amines. The (+) isomer of pseudoephedrine is known to be a sympathomimetic amine which is sold as a decongestant under the trade name SUDAFED®. (−)-Phenylephrine (Neo-Synephrine®) and (−)-ephedrine are also known to be sympathomimetic amines which act as decongestants.

Methods:

Membrane Preparations.

PULMONARY ALPHA-1 AND BETA-2 RECEPTORS: The lungs of mongrel dogs were separated from cartilaginous airways and major blood vessels, weighed, chopped and placed into 10 volumes of ice-cold buffered sucrose (50 mM Tris-HCl pH 7.4, 1 mM EGTA, 0.32M Sucrose). The tissue was then homogenized in a Polytron tissue homogenizer. The homogenate was filtered through two layers of cheesecloth, and the filtrate was dounced three times using a Con-Turque Potter homogenizer. The dounced filtrate was centrifuged at 1000×g for 15 min at 4° C. The supernatant was recentrifuged at 30,000×g for 30 min at 4° C. and the resulting pellet was washed and resuspended in 10 volumes of Tris buffer (50 mM Tris HCl, pH 7.4, 1 mM EGTA) and incubated at 37° C. for 30 min in a shaking water bath. The suspension was centrifuged at 4° C. at 30,000×g for 30 min and the resulting pellet washed in 10 volumes of Tris buffer. The final pellet was resuspended in 0.5 volume of 50 mM Tris HCl, pH 7.4, 1 mM EGTA, 25 mM $MgCl_2$. Protein concentration was then determined by the Lowry method and the final suspension was adjusted to 10 mg of protein/ml, aliquoted and stored at 90° C.

Particulates were also prepared for $\beta_2$ receptors using the identical procedure except the final protein concentration was adjusted to 0.1 mg/ml.

BRAIN ALPHA-2 RECEPTORS: Membranes of mongrel dogs were harvested from the canine frontal cortex and prepared as described for lung except that the final membrane protein concentration was adjusted to 0.5 mg/ml.

Binding Assays.

ALPHA-1 BINDING, $^3$H-PRAZOCIN: Canine lung membrane preparations (500 ug protein/100 ul) were incubated with $^3$H-Prazocin (77.9 Ci/mmol) for 60 min at 25° C. in a final volume of 0.25 ml of buffer (50 mM Tris-HCl/1 mM EGTA, pH 7.4). Each experimental point was determined in triplicate. Nonspecific binding was determined separately for each concentration point using 10 μM phentolamine. The final concentration of $^3$H-Prazocin was 0.7–1.1 nM in competition studies and between 0.1 and 10 nM in saturation experiments. All binding assay incubations were terminated by rapid dilution with 2 ml of ice-cold wash buffer (50 nM Tris-HCl, pH 7.4) and filtration through Whatman GF/B filters using a Brandel receptor-binding harvester. The filters were washed twice more with 4 ml of wash buffer and then added to 6 ml Cytoscint (ICN, Costa Mesa Calif.) for liquid scintillation counting (Barnes et al., 1983). In all experiments less than 17% of the added radio ligand was bound, and specific binding was about 65–70% of total binding.

ALPHA-2 BINDING $^{125}$IODOCLONIDINE. Canine brain membranes (50 μg protein/100 ul) were incubated with p-iodoclonidine (2200 Ci/mmol) for 120 min at 25° C. in a final volume of 0.25 ml. Nonspecific binding was determined in separate incubations in the presence of 10 μM phentolamine. The final concentration of p-iodoclonidine was 44–45 pM in competition studies and between 50 pM and 10 nM in saturation experiments. Bound and free p-$^{125}$iodoclonidine were separated and the bound quantified as described above for the ICYP assays. An average of 6% of radioligand was bound, and specific binding was about 91% of total binding. BETA-2 BINDING, $^{125}$IODOCYANOPINDOLOL ($^{125}$ICYP). Canine lung membranes (10 μg protein/100 ul) were incubated with $^{125}$ICYP (2200 Ci/mmol) for 110 min at 30° C. in a final volume of 0.25 ml. Nonspecific binding was determined in separate incubations in the presence of 2 μM d,l-propranolol. Each experimental point was determined in triplicate. The final concentration of $^{125}$ICYP was 8–12 pM in competition studies and between 2 and 200 pM in saturation experiments. Incubations were terminated as described above for the $\alpha_1$ assays. Filters were placed into polyethylene tubes and the bound ligand was determined by gamma spectrometry (Sano et al., 1993). An average of 27% of radio ligand was bound, and specific binding was about 90% of total binding.

All data were analyzed with the aid of microcomputer nonlinear curve fitting programs (PRISM 2.0, Graphpad Software, San Diego Calif.).

Results:

The receptors resident in each of the three membrane preparations were evaluated by standard saturation analysis following the addition of increasing concentrations of the appropriate radioligand. In the case of the $\alpha_1$- and $\beta_2$-assays the mathematical analysis was consistent with a one site fit. The $\alpha_2$-receptor analysis was best fit as two sites, one high and one low affinity. The radio ligand added for subsequent $\alpha_2$-displacement assays was adjusted to evaluate only the high affinity receptor. Contributions from p-iodoclonidine binding to imidazoline receptors in the $\alpha_2$-displacement assay were evaluated with epinephrine. Epinephrine easily displaced all bound p-iodoclonidine which indicates that at the concentrations employed, p-iodoclonidine labeled few if any imidazoline receptors. Similarly, with the $\beta_2$-assay, contributions from the binding of ICYP to $\beta_1$ sites was evaluated with the $\beta_1$-selective antagonist, atenolol. Atenolol was largely ineffective in displacing ICYP from pulmonary membranes indicating little if any $\beta_1$ binding within the assay. All subsequent analyses with displacement by individual test compounds used the Kd determined from the saturation analysis since it is generally considered a more reliable estimate of the true equilibrium dissociation constant.

Table 1 provides the binding characteristics of the $\alpha_1$-receptors in the membrane preparation for prazocin. The Kd is the apparent equilibrium dissociation constant for prazocin. The BMAX is the number of $\alpha_1$-receptor binding sites for prazocin in this membrane preparation expressed as femtomoles per mg protein.

TABLE 1

$\alpha_1$-Receptor Binding Characteristics
(canine lung membranes)

| Measure | Summary |
|---|---|
| Scatchard Analysis | |
| Kd | 0.84 nM |
| BMAX | 55 |
| Saturation Analysis | |
| Kd | 0.73 nM |
| BMAX | 53 |

Table 2 provides the binding characteristics of the $\alpha_2$-receptors in the membrane preparation for p-iodoclonidine. The Kd is the apparent equilibrium dissociation constant for p-iodoclonidine. The BMAX is the number of $\alpha_2$-receptor binding sites for p-iodoclonidine in this membrane preparation expressed as femtomoles per mg protein. Note that the two site data from the Saturation Analysis is more reliable than the Scatchard Analysis because the Scatchard Analysis assumes only one site. In order to obtain both values from the Scatchard plots, the points in the transition zone were divided and assigned to high and low affinity plots.

TABLE 2

$\alpha_2$-Receptor Binding Characteristics
(canine cerebral cortex membranes)

| Measure | Summary |
|---|---|
| Scatchard Analysis | |
| $Kd_1$ (high affinity) | 0.15 nM |
| $Kd_2$ (low affinity) | 0.87 nM |
| $BMAX_1$ (high affinity) | 67 |
| $BMAX_2$ (low affinity) | 120 |
| Saturation Analysis | |
| $Kd_1$ (high affinity) | 0.15 nM |
| $Kd_2$ (low affinity) | 3.01 nM |
| $BMAX_1$ (high affinity) | 57 |
| $BMAX_2$ (low affinity) | 73 |

Table 3 provides the binding characteristics of the $\beta_2$-receptors in the membrane preparation for $^{125}$iodocyanopindolol (ICYP). The Kd is the apparent equilibrium dissociation constant for ICYP. The BMAX is the number of $\beta_2$-receptor binding sites for ICYP in this membrane preparation expressed as femtomoles per mg protein.

TABLE 3

$\beta_2$-Receptor Binding characteristics (canine lung membranes)

| Measure | Run 1 | Run 2 | Summary |
|---|---|---|---|
| Scatchard Analysis | | | |
| Kd | 9.9 pM | 7.8 pM | 8.9 pM |
| BMAX | 150 | 139 | 145 |
| Saturation Analysis | | | |
| Kd | 9.6 pM | 9.3 pM | 9.5 pM |
| BMAX | 149 | 142 | 146 |

The concentration of test drug required to inhibit 50% of specific prazocin, p-iodoclonidine or ICYP binding ($IC_{50}$) is provided in Table 4. The Ki values of $\alpha_1$, $\alpha_2$ and $\beta_2$-receptors for each drug are also provided in Table 4, where the Ki is $IC_{50}+(1+I/Kd)$. The variable, I, is the concentration of tracer added and the variable, Kd, is the equilibrium dissociation constant empirically determined for this receptor population.

TABLE 4

| Drugs | Alpha-1 | | Alpha-2 | | Beta-2 | | Ki-Ratio | | |
|---|---|---|---|---|---|---|---|---|---|
| | $IC_{50}$ | $K_i$ | $IC_{50}$ | $K_i$ | $IC_{50}$ | $K_i$ | $\alpha1/\alpha2$ | $\alpha1/\beta2$ | $\beta2/\alpha2$ |
| (+)-Pseudoephedrine | 691 | 299 | 28 | 21 | 502 | 220 | 14.23 | 1.35 | 10.48 |
| (−)-Pseudoephedrine | 98 | 48 | 6.0 | 4.6 | 542 | 237 | 10.43 | 0.20 | 51.52 |
| (+)-Ephedrine | 92 | 40 | 31 | 24 | 1361 | 614 | 1.67 | 0.07 | 25.6 |
| (−)-Ephedrine | 109 | 47 | 0.77 | 0.59 | 12 | 5 | 79.67 | 9.40 | 8.47 |
| (+)-Phenylpropanolamine | 1464 | 612 | 15 | 12 | 486 | 215 | 51.00 | 2.85 | 17.92 |
| (−)-Phenylpropanolamine | 116 | 48 | 0.31 | 0.24 | 50 | 22 | 200.00 | 2.18 | 91.67 |
| (+)-Phenylephrine | 178 | 68 | 0.82 | 0.63 | 119 | 55 | 107.93 | 1.24 | 87.30 |
| (−)-Phenylephrine | 7 | 3 | 0.02 | 0.015 | 10 | 5 | 200.00 | 0.60 | 333.33 |
| (+)-Norpseudoephedrine | 351 | 138 | 5 | 4 | 325 | 87 | 27.6 | 1.59 | 21.75 |
| (−)-Norpseudoephedrine | 668 | 274 | 10 | 8 | 187 | 149 | 34.25 | 0.007 | 18.63 |

Example 1 shows the stereochemical structures of the compounds in Table 4. Correlation of those structures with the binding activity data provided in Table 4 reveals which molecular configurations have higher affinity for adrenergic receptors.

For example, the only difference between (−)-ephedrine and (+)-pseudoephedrine is the chiral configuration of the first chiral carbon atom in the side chain. In (−)-ephedrine, the center is in the (R) configuration, whereas in (+)-pseudoephedrine the chiral center is in the (S) configuration. All other atoms, bond lengths and spatial geometries in these two molecules are identical. Therefore comparison of the $IC_{50}$ values for binding of these stereoisomers to $\alpha$-1, $\alpha$-2 and $\beta$-2 receptors reveals the spatial preference of the receptors. The $IC_{50}$ value for (−)-ephedrine binding to $\alpha_1$ receptors is 109 nm/ml. For (+)-pseudoephedrine, the $IC_{50}$ value for binding to $\alpha_1$ receptors is 691 nm/ml. (−)-Ephedrine therefore binds with greater affinity, indicating that the (R) configuration is preferred by this receptor. Five such comparisons are possible from this data set for each of the three receptors. These comparisons are provided in Table 5.

TABLE 5

Most potent configuration ("R" or "S") in the first chiral center*

| Comparison | Receptors | | |
|---|---|---|---|
| | $\alpha_1$ | $\alpha_2$ | $\beta_2$ |
| (−)-ephedrine/(+)-pseudoephedrine | R | R | R |
| (−)-pseudoephedrine/(+)-ephedrine | = | R | R |
| (−)-phenylpropanolamine/(−)-norpseudoephedrine | R | R | R |
| (+)-norpseudoephedrine/(+)-phenylpropanolamine | R | R | = |
| (+)-phenylephrine/(−)-phenylephrine | R | R | R |

*If the $IC_{50}$ values are within 50%, an "=" sign was assigned.

Of the fifteen comparisons in Table 5, thirteen of the most potent binding agents are in the R-configuration. In two instances there is little difference between the binding potency of the R- and S-configurations. None of the more potent binding agents is in the S-configuration (p<0.01, Binomial Test). The results are observed for each of the ephedrine, phenylpropanolamine and phenylephrine families of compounds examined. The results are also observed for each of the three different types of adrenergic receptors ($\alpha_1$, $\alpha_2$ and $\beta_2$).

In Table 6, the potency of binding to adrenergic receptors is correlated with the molecular configuration at the second chiral center. Only twelve comparisons were made in this table because the two phenylephrine enantiomers have only one chiral center. In only one case does an R-configured molecule bind with greater affinity than does its S-counterpart. In three cases the R- and S-configured molecules bind with similar affinity. However, in the majority of cases (eight), the S-configuration is preferred (p<0.05, Binomial Test). These results therefore indicate that the S-configuration in the second chiral center is preferred by $\alpha_1$, $\alpha_2$ and $\beta_2$ receptors.

TABLE 6

Most potent configuration ("R" or "S") in the second chiral center*

| Comparison | Receptors | | |
|---|---|---|---|
| | $\alpha_1$ | $\alpha_2$ | $\beta_2$ |
| (−)-ephedrine/(+)-pseudoephedrine | = | S | S |
| (−)-pseudoephedrine/(+)-ephedrine | R | = | S |

TABLE 6-continued

Most potent configuration ("R" or "S") in the second chiral center*

| Comparison | Receptors | | |
|---|---|---|---|
| | $\alpha_1$ | $\alpha_2$ | $\beta_2$ |
| (−)-phenylpropanolamine/(−)-norpseudoephedrine | S | S | S |
| (+)-norpseudoephedrine/(+)-phenylpropanolamine | S | = | S |
| (+)-phenylephrine/(−)-phenylephrine | na | na | na |

*If the $IC_{50}$ values are within 50%, an "=" sign was assigned.

These comparisons indicate that an (R) chiral configuration for the first chiral center and an (S) for the second chiral center are preferred, for the most potent binding. Interestingly, in this R,S-stereoisomeric structure, both constituents at the R- and S-chiral centers extend in the same direction—above the plane of the schematic drawing. See Example 1.

In Table 7 the binding potency of sympathomimetic amines with free terminal amines is compared to the binding potency of sympathomimetic amines having a methylated terminal amine. In this comparison, the free amine is preferred no more frequently than the methylated amine, indicating no preference exists for a free amine versus a methylated amine.

TABLE 7

Effect of Terminal Methylated Amine ("M") or Free Amine ("A")*

| Comparison | Receptors | | |
|---|---|---|---|
| (A = free amine/M = methylated amine) | $\alpha_1$ | $\alpha_2$ | $\beta_2$ |
| (−)-ephedrine/(−)phenylpropanolamine | = | M | A |
| (+)-pseudoephedrine/(−)-norpseudoephedrine | = | M | M |
| (−)-pseudoephedrine/(+)-norpseudoephedrine | A | = | = |
| (+)-ephedrine/(+)-phenylpropanolamine | A | = | = |

*If the IC50 values were within 50%, an "=" sign was assigned.

EXAMPLE 3

Pupil Dilation and Intraocular Pressure

The ability of the present stereoisomers to induce pupil dilation (mydriasis) was compared to the pupil induction of known mydriatic agents. The (+)-stereoisomer of pseudoephedrine and the (−)-enantiomer of phenylephrine are known to be a mydriatic agents.

Methods:

The following stereoisomers were evaluated for their efficacy in producing mydriasis and for their effects on intraocular pressure (IOP): (+)-pseudoephedrine, (−)-pseudoephedrine, (+)-ephedrine, (−)-ephedrine, (+)-phenylpropanolamine, (−) phenylpropanolamine, (+)-norpseudoephedrine, (−)-norpseudoephedrine and metaraminol bitartrate salt. These diastereomers were administered topically as either 1% or 2% solutions in buffered saline. Pupillary diameter and IOP were measured in all animals over a six hour time period during the day to minimize diurnal variations in IOP and pupil diameter.

The experiments were performed on adult male New Zealand white rabbits weighing 3.0–6.0 kg. All rabbits were caged individually and maintained on a 12 hr/12 hr light/dark schedule with free access to food and water. All animal procedures were in conformity with the ARVO Resolution on the Use and Care of Animals in Research. All treated rabbits had served as controls by having received a saline treatment on a different day.

Drug or saline-control solutions were applied to the superior aspect of the globe in a volume of 25 μl and allowed to spread over the cornea and sclera, while a conjunctival trough was formed by retracting the lower eyelid for approximately 30 seconds. Only one eye received drug treatment. The contralateral eye served as a control. Saline (or PBS) and drug treated rabbits were treated and observed simultaneously. A single dose was given at time zero and IOP and pupil diameter measured at −1.0, −0.5, 0.5, 1, 3 and 5 hrs post-treatment.

IOP measurements were recorded with an Alcon Applanation Pneumotonograph (Surgical Products Division, Alcon Laboratories, Inc., Ft. Worth, Tex.) in rabbits placed in Lucite restraining cages. Initial topical application of a two drop 0.5% proparacaine HCl (Ophthetic®, Allergan Pharmaceuticals, Inc.) was performed on each rabbit.

Pupil diameter was measured visually at the point of the greatest horizontal diameter with a transparent millimeter ruler. All measurements were made under the identical ambient lighting conditions.

Mean and Standard Error values were used to construct time-response and dose-response curves for the treated and contralateral eye of research rabbits. The data were analyzed statistically by an analysis of variance and a Bonferoni's test for significance. P<0.05 was the accepted level of significance.

Results:

Although some variation in baseline IOP was noted among the total rabbits tested, there were no significant changes in IOP or pupil diameter (PD) in the saline control groups (Tables 8 & 9) during the six hour time period selected for drug testing.

The adrenergic agonist (+)-pseudoephedrine is known to be an active sympathomimetic amine which has both direct and indirect α- and β-agonist activity. In this study, (+)-pseudoephedrine produced mydriasis in only the treated eye. A slight acute elevation in IOP in the treated eye was observed following 1% and 2% topical application of (+)-pseudoephedrine. A delayed elevation in IOP was also observed in the contralateral eye. (Table 8).

(−)-Pseudoephedrine produced some mild mydriasis at the two doses tested but had little effect on IOP (Tables 8 & 9). $\alpha_1$-Receptor binding studies have indicated that (−)-pseudoephedrine is six to seven times more potent than (+)-pseudoephedrine. However, the mydriatic responses observed for these two agents were similar. The absence of an IOP effect for (−)-pseudoephedrine may be due to its ability to stimulate a, receptors in the outflow pathway, which would oppose an increase in IOP.

(+)-Ephedrine is also known to stimulate both α and β-adrenergic receptors and to have pronounced cardiovascular effects when administered systemically. Topically, (+)-ephedrine produced significant mydriasis and an elevation in IOP in the treated eye (Tables 8 & 9). Although the IOP changed at the higher 2% dose, pupil diameter was unchanged.

(−)-Ephedrine had no effect on pupil diameter at either of the doses tested despite an increase in IOP. These data suggest that the IOP effects and pupil diameter may be mediated through different $\alpha_1$ receptors.

(−)-Phenylpropanolamine belongs to the norephedrine series of compounds and, like ephedrine, has both direct and indirect adrenergic actions. This compound produced a significant and prolonged mydriatic response, while causing only a mild rise in IOP (not significant) (Tables 8 & 9). Its corresponding enantiomer, (+)-phenylpropanolamine, was much less effective (Tables 8 & 9).

Similarly, (+)- and (−)-norpseudoephedrine caused significant mydriasis but gave rise to an accompanying increase in IOP (Tables 8 & 9).

Metaraminol, a compound similar to ephedrine which also has both direct and indirect sympathomimetic activity, produced mydriasis with an accompanying increase in IOP (Tables 8 & 9).

TABLE 8

IOP in mmHg

| | | Time in Hr. | | | | | |
|---|---|---|---|---|---|---|---|
| | | −1 | −0.5 | 0.5 | 1 | 3 | 5 |
| SALINE (15) | U | 27 ± 0.9 | 25 ± 0.4 | 26 ± 1.5 | 25 ± 1.4 | 27 ± 0.9 | 26 ± 1.2 |
| | T | 26 ± 0.9 | 25 ± 1.1 | 26 ± 1.1 | 25 ± 1.3 | 27 ± 0.8 | 26 ± 0.8 |
| SALINE (15) | U | 20 ± 0.7 | 19 ± 0.9 | 20 ± 1.0 | 19 ± 1.0 | 20 ± 1.0 | 19 ± 1.1 |
| | T | 19 ± 0.8 | 18 ± 0.9 | 18 ± 0.8 | 17 ± 0.7 | 19 ± 0.9 | 18 ± 1.1 |
| DRUG (1%) | | | | | | | |
| (+)-Pseudoephedrine | U | 19 ± 1.0 | 18 ± 1.6 | 18 ± 2.0 | 19 ± 1.2 | 20 ± 2.0 | 21 ± 0.9 |
| | T | 20 ± 0.2 | 20 ± 1.7 | 19 ± 2.3 | 22 ± 1.4 | 21 ± 2.0 | 23 ± 2.3 |
| (−)-Pseudoephedrine | U | 21 ± 1.6 | 20 ± 1.4 | 21 ± 1.4 | 19 ± 1.3 | 19 ± 1.0 | 18 ± 1.1 |
| | T | 23 ± 1.8 | 24 = 1.7 | 25 ± 0.5 | 24 ± 1.0 | 22 ± 0.6 | 21 ± 0.7 |
| (+)-Ephedrine | U | 20 ± 1.5 | 19 ± 1.8 | 19 ± 1.3 | 20 ± 2.1 | 21 ± 1.8 | 22 ± 1.5 |
| | T | 21 ± 0.7 | 20 ± 1.9 | 25 ± 1.6 | 25 ± 1.4 | 22 ± 0.8 | 23 ± 1.9 |
| (−)-Ephedrine | U | 19 ± 1.7 | 17 ± 1.0 | 20 ± 1.9 | 19 ± 1.2 | 16 ± 0.9 | 15 ± 1.5 |
| | T | 22 ± 2.0 | 23 ± 0.9 | 23 ± 2.5 | 26 ± 1.0 | 25 ± 0.6 | 23 ± 0.9 |
| (−)-Phenylpropanolamine | U | 23 ± 2.1 | 21 ± 2.3 | 27 ± 2.0 | 25 ± 0.9 | 25 ± 1.9 | 22 ± 1.3 |
| | T | 25 ± 0.2 | 22 ± 1.6 | 25 ± 2.7 | 25 ± 2.2 | 23 ± 2.6 | 24 ± 3.4 |
| (+)-Phenylpropanolanime | U | 23 ± 0.9 | 22 ± 1.3 | 21 ± 1.2 | 22 ± 1.1 | 23 ± 1.5 | 22 ± 1.0 |
| | T | 25 ± 1.2 | 22 = 1.7 | 25 ± 0.7 | 24 ± 1.2 | 22 ± 1.2 | 21 ± 0.7 |
| (−)-Phenylephrine | U | 16 ± 1.0 | 15 ± 2.1 | 18 ± 1.6 | 19 ± 1.3 | 20 ± 1.9 | 19 ± 1.7 |
| | T | 20 ± 1.6 | 16 ± 1.5 | 24 ± 0.6 | 24 ± 1.0 | 23 ± 1.5 | 21 ± 1.9 |
| (+)-Phenylephrine | U | 21 ± 2.0 | 19 ± 2.0 | 19 ± 1.8 | 17 ± 1.1 | 16 ± 1.0 | 17 ± 1.7 |
| | T | 19 ± 1.8 | 18 ± 2.1 | 16 ± 1.5 | 16 ± 0.7 | 15 ± 0.5 | 16 ± 1.0 |
| (−)-Norpseudoephedrine | U | 17 ± 1.5 | 20 ± 1.7 | 21 ± 1.0 | 18 ± 1.6 | 20 ± 1.9 | 23 ± 0.9 |

TABLE 8-continued

| | | IOP in mmHg | | | | | |
| --- | --- | --- | --- | --- | --- | --- | --- |
| | | Time in Hr. | | | | | |
| | | −1 | −0.5 | 0.5 | 1 | 3 | 5 |
| | T | 17 ± 1.0 | 18 ± 1.6 | 17 ± 1.0 | 17 ± 1.5 | 21 ± 1.6 | 18 ± 1.0 |
| (+)-Norpseudoephedrine | U | 20 ± 1.7 | 21 = 1.7 | 24 ± 1.8 | 19 ± 1.8 | 18 ± 2.8 | 17 ± 2.8 |
| | T | 18 ± 1.0 | 19 = 2.3 | 19 ± 2.4 | 18 ± 1.8 | 18 ± 2.0 | 17 ± 2.8 |
| Metaraminol Bitartate | U | 18 ± 1.4 | 16 ± 1.1 | 18 ± 1.7 | 18 ± 1.0 | 19 ± 1.4 | 17 ± 0.8 |
| Salt, USP | T | 21 ± 2.3 | 19 ± 1.3 | 25 ± 1.2 | 24 ± 1.3 | 21 ± 2.8 | 21 ± 2.7 |
| Mephentermine | U | 17 ± 1.1 | 17 ± 1.0 | 20 ± 2.1 | 17 ± 1.6 | 20 ± 1.4 | 17 ± 1.5 |
| Hemisulfate Salt | T | 19 ± 1.7 | 18 ± 1.8 | 24 ± 1.0 | 24 ± 0.7 | 22 ± 0.9 | 18 ± 1.6 |
| DRUG (2%) | | | | | | | |
| (+)-Pseudoephedrine | U | 20 ± 1.0 | 16 ± 10 | 18 ± 2.3 | 17 ± 2.1 | 18 ± 1.2 | 22 ± 1.4 |
| | T | 24 ± 1.1 | 18 ± 1.4 | 26 ± 0.8 | 23 ± 1.3 | 22 ± 2.1 | 23 ± 2.4 |
| (−)-Pseudoephedrine | U | 18 ± 1.0 | 15 ± 1.0 | 18 ± 2.0 | 16 ± 1.2 | 17 ± 1.1 | 16 ± 0.6 |
| | T | 22 ± 1.0 | 18 ± 1.2 | 17 ± 1.2 | 19 ± 1.8 | 17 ± 1.2 | 18 ± 1.7 |
| (+)-Ephedrine | U | 19 ± 1.8 | 18 ± 1.2 | 18 ± 2.0 | 18 ± 1.1 | 17 ± 2.2 | 16 ± 0.8 |
| | T | 20 ± 2.0 | 19 ± 1.8 | 25 ± 1.7 | 25 ± 1.7 | 20 ± 1.5 | 17 ± 0.8 |
| (−)-Ephedrine | U | 17 ± 1.2 | 19 ± 0.9 | 19 ± 1.4 | 19 ± 1.9 | 18 ± 0.7 | 19 ± 1.5 |
| | T | 16 ± 2.0 | 16 ± 0.7 | 16 ± 1.0 | 15 ± 0.4 | 17 ± 0.7 | 19 ± 0.8 |
| (−)-Phenylpropanolamine | U | 17 ± 2.1 | 17 ± 1.4 | 19 ± 2.9 | 20 ± 1.7 | 22 ± 1.9 | 19 ± 1.2 |
| | T | 18 ± 2.0 | 16 ± 1.3 | 21 ± 1.9 | 21 ± 1.9 | 21 ± 1.7 | 20 ± 2.1 |
| (+)-Phenylpropanolamine | U | 21 ± 1.0 | 20 ± 1.4 | 19 ± 1.5 | 17 ± 0.3 | 17 ± 1.0 | 15 ± 0.7 |
| | T | 24 ± 1.2 | 23 = 1.4 | 24 ± 0.9 | 27 ± 0.9 | 20 ± 1.8 | 18 ± 1.0 |
| (−)-Phenylephrine | U | 17 ± 1.9 | 17 ± 1.9 | 20 ± 2.0 | 20 ± 2.4 | 14 ± 1.7 | 14 ± 2.0 |
| | T | 18 ± 1.6 | 15 ± 1.5 | 12 ± 0.8 | 14 ± 2.0 | 16 ± 0.8 | 14 ± 1.3 |
| (+)-Phenylephrine | U | 19 ± 1.6 | 19 ± 2.2 | 21 ± 1.7 | 22 ± 2.2 | 20 ± 1.8 | 18 ± 1.9 |
| | T | 19 ± 0.9 | 19 ± 0.8 | 20 ± 1.7 | 19 ± 1.8 | 19 ± 2.2 | 16 ± 2.4 |
| (−)-Norpseudoephedrine | U | 16 ± 1.0 | 17 ± 0.7 | 16 ± 1.2 | 19 ± 1.2 | 22 ± 1.5 | 21 ± 1.1 |
| | T | 16 ± 1.9 | 15 ± 0.9 | 15 ± 0.5 | 18 ± 0.7 | 18 ± 1.1 | 18 ± 1.4 |
| (+)-Norpseudoephedrine | U | 18 ± 2.6 | 19 ± 2.5 | 22 ± 2.0 | 23 ± 2.1 | 22 ± 2.7 | 24 ± 2.3 |
| | T | 19 ± 2.4 | 16 ± 2.5 | 18 ± 2.5 | 20 ± 2.3 | 20 ± 2.0 | 21 ± 2.8 |
| Metaraminol Bitartate | U | 17 ± 1.2 | 15 ± 0.7 | 19 ± 1.1 | 18 ± 0.8 | 19 ± 1.1 | 21 ± 1.6 |
| Salt, USP | T | 15 ± 0.7 | 14 ± 0.9 | 15 ± 1.1 | 16 ± 3.6 | 14 ± 2.0 | 13 ± 0.8 |
| Mephentermine | U | 18 ± 2.2 | 17 ± 2.1 | 18 ± 1.6 | 16 ± 1.0 | 18 ± 0.8 | 20 ± 1.7 |
| Hemisulfate Salt | T | 21 ± 2.3 | 19 ± 2.0 | 23 ± 2.2 | 23 ± 2.2 | 21 ± 2.3 | 23 ± 1.5 |

Results are as mean ± S.E. of five-six rabbits per drug.
U = Untreated contralateral eye
T = Drug treated eye

TABLE 9

| | | Pupil Diameter in mm | | | | | |
| --- | --- | --- | --- | --- | --- | --- | --- |
| | | Time in Hr. | | | | | |
| | | −1 | −0.5 | 0.5 | 1 | 3 | 5 |
| SALINE | U | 5 ± 0.2 | 5 ± 0.2 | 5 ± 0.2 | 5 ± 0.2 | 5 ± 0.2 | 5 ± 0.2 |
| (15) | T | 5 ± 0.2 | 5 ± 0.2 | 5 ± 0.2 | 5 ± 0.2 | 5 ± 0.2 | 5 ± 0.2 |
| SALINE | U | 5 ± 0.2 | 5 ± 0.2 | 5 ± 0.2 | 5 ± 0.2 | 5 ± 0.2 | 5 ± 0.2 |
| (15) | T | 5 ± 0.2 | 5 ± 0.2 | 5 ± 0.2 | 5 ± 0.2 | 5 ± 0.2 | 5 ± 0.2 |
| DRUG (1%) | | | | | | | |
| (+)-Pseudoephedrine | U | 6 ± 0.4 | 6 ± 0.4 | 6 ± 0.4 | 6 ± 0.4 | 6 ± 0.4 | 6 ± 0.4 |
| | T | 7 ± 0.2 | 7 ± 0.2 | 8 ± 0.2 | 8 ± 0.2 | 8 ± 0.2 | 8 ± 0.2 |
| (−)-Pseudoephedrine | U | 7 ± 0.2 | 7 ± 0.2 | 7 ± 0.2 | 7 ± 0.2 | 7 ± 0.2 | 7 ± 0.2 |
| | T | 7 ± 0.2 | 7 ± 0.2 | 8 ± 0.2 | 8 ± 0.2 | 8 ± 0.2 | 8 ± 0.2 |
| (+)-Ephedrine | U | 6 ± 0.4 | 6 ± 0.4 | 6 ± 0.4 | 6 ± 0.4 | 6 ± 0.4 | 6 ± 0.4 |
| | T | 6 ± 0.4 | 6 ± 0.4 | 9 ± 0.4 | 9 ± 0.4 | 9 ± 0.4 | 9 ± 0.4 |
| (−)-Ephedrine | U | 6 ± 0.4 | 6 ± 0.4 | 6 ± 0.4 | 6 ± 0.4 | 6 ± 0.4 | 6 ± 0.4 |
| | T | 6 ± 0.4 | 6 ± 0.4 | 6 ± 0.4 | 6 ± 0.4 | 6 ± 0.4 | 6 ± 0.4 |
| (−)-Phenylpropanolamine | U | 7 ± 0.4 | 7 ± 0.4 | 7 ± 1.2 | 7 ± 1.2 | 7 ± 1.2 | 7 ± 1.2 |
| | T | 7 ± 0.5 | 7 ± 0.5 | 10 ± 0.2 | 10 ± 0.2 | 10 ± 0.2 | 10 ± 0.2 |
| (+)-Phenylpropanolamine | U | 7 ± 0.3 | 7 ± 0.3 | 7 ± 0.3 | 7 ± 0.4 | 7 ± 0.4 | 7 ± 0.3 |
| | T | 7 ± 0.3 | 7 ± 0.3 | 8 ± 0.3 | 8 ± 0.4 | 8 ± 0.4 | 7 ± 0.5 |
| (−)-Phenylephrine | U | 6 ± 0.4 | 6 ± 0.4 | 6 ± 0.4 | 6 ± 0.4 | 6 ± 0.4 | 6 ± 0.4 |
| | T | 6 ± 0.4 | 6 ± 0.4 | 7 ± 0.4 | 9 ± 0.4 | 9 ± 0.4 | 9 ± 0.4 |
| (+)-Phenylephrine | U | 5 ± 0.2 | 5 ± 0.2 | 6 ± 0.2 | 9 ± 0.2 | 9 ± 0.2 | 9 ± 0.2 |
| | T | 5 ± 0.2 | 5 ± 0.2 | 6 ± 0.2 | 9 ± 0.2 | 9 ± 0.2 | 9 ± 0.2 |
| (−)-Norpseudoephedrine | U | 5 ± 0.2 | 5 ± 0.2 | 6 ± 0.2 | 6 ± 0.2 | 6 ± 0.2 | 6 ± 0.2 |
| | T | 5 ± 0.2 | 5 ± 0.2 | 6 ± 0.2 | 6 ± 0.2 | 6 ± 0.2 | 6 ± 0.2 |

TABLE 9-continued

Pupil Diameter in mm

| | | Time in Hr. | | | | | |
|---|---|---|---|---|---|---|---|
| | | −1 | −0.5 | 0.5 | 1 | 3 | 5 |
| (+)-Norpseudoephedrine | U | 6 ± 0.2 | 6 ± 0.2 | 8 ± 0.2 | 8 ± 0.2 | 8 ± 0.2 | 8 ± 0.2 |
| | T | 6 ± 0.2 | 6 ± 0.2 | 8 ± 0.2 | 8 ± 0.2 | 8 ± 0.2 | 8 ± 0.2 |
| Metaraminol Bitartrate | U | 7 ± 0.5 | 7 ± 0.5 | 7 ± 0.5 | 7 ± 0.5 | 7 ± 0.5 | 7 ± 0.5 |
| Salt, USP | T | 7 ± 0.5 | 7 ± 0.5 | 9 ± 0.5 | 9 ± 0.5 | 9 ± 0.2 | 9 ± 0.5 |
| Mephentermine | U | 7 ± 0.2 | 7 ± 0.2 | 7 ± 0.2 | 7 ± 0.2 | 7 ± 0.2 | 7 ± 0.2 |
| Hemisulfate Salt | T | 7 ± 0.2 | 7 ± 0.2 | 10 ± 0.2 | 10 ± 0.2 | 10 ± 0.2 | 10 ± 0.2 |
| DRUG (2%) | | | | | | | |
| (+)-Pseudoephedrine | U | 6 ± 0.4 | 6 ± 0.4 | 6 ± 0.4 | 6 ± 0.4 | 6 ± 0.4 | 6 ± 0.4 |
| | T | 6 ± 0.4 | 6 ± 0.4 | 7 ± 0.4 | 7 ± 0.4 | 7 ± 0.4 | 7 ± 0.4 |
| (−)-Pseudoephedrine | U | 7 ± 0.4 | 7 ± 0.4 | 7 ± 0.4 | 7 ± 0.4 | 7 ± 0.4 | 7 ± 0.4 |
| | T | 7 ± 0.4 | 7 ± 0.4 | 8 ± 0.4 | 8 ± 0.4 | 8 ± 0.4 | 10 ± 0.4 |
| (+)-Ephedrine | U | 7 ± 0.2 | 7 ± 0.2 | 7 ± 0.2 | 7 ± 0.2 | 7 ± 0.2 | 7 ± 0.2 |
| | T | 7 ± 0.2 | 7 ± 0.2 | 7 ± 0.2 | 7 ± 0.2 | 7 ± 0.2 | 7 ± 0.2 |
| (−)-Ephedrine | U | 5 ± 0.2 | 5 ± 0.2 | 9 ± 0.2 | 9 ± 0.2 | 9 ± 0.2 | 9 ± 0.2 |
| | T | 5 ± 0.2 | 5 ± 0.2 | 9 ± 0.2 | 9 ± 0.2 | 9 ± 0.2 | 9 ± 0.2 |
| (−)-Phenylpropanolamine | U | 5 ± 0.5 | 5 ± 0.5 | 5 ± 0.5 | 5 ± 0.5 | 5 ± 0.5 | 5 ± 0.5 |
| | T | 5 ± 0.5 | 5 ± 0.5 | 6 ± 0.5 | 8 ± 0.5 | 8 ± 0.5 | 8 ± 0.5 |
| (+)-Phenylpropanolamine | U | 6 ± 0.4 | 6 ± 0.4 | 7 ± 0.7 | 7 ± 0.5 | 7 ± 0.5 | 7 ± 0.7 |
| | T | 6 ± 0.4 | 6 ± 0.4 | 8 ± 0.4 | 8 ± 0.4 | 8 ± 0.4 | 8 ± 0.4 |
| (−)-Phenylephrine | U | 6 ± 0.2 | 6 ± 0.2 | 12 ± 0.2 | 12 ± 0.2 | 12 ± 0.2 | 12 ± 0.2 |
| | T | 6 ± 0.2 | 6 ± 0.2 | 12 ± 0.2 | 12 ± 0.2 | 12 ± 0.2 | 12 ± 0.2 |
| (+)-Phenylephrine | U | 5 ± 0.2 | 5 ± 0.2 | 6 ± 0.2 | 9 ± 0.2 | 9 ± 0.2 | 9 ± 0.2 |
| | T | 5 ± 0.2 | 5 ± 0.2 | 6 ± 0.2 | 9 ± 0.2 | 9 ± 0.2 | 9 ± 0.2 |
| (−)-Norpseudoephedrine | U | 6 ± 0.4 | 6 ± 0.4 | 9 ± 0.4 | 9 ± 0.4 | 9 ± 0.4 | 9 ± 0.4 |
| | T | 6 ± 0.4 | 6 ± 0.4 | 9 ± 0.4 | 9 ± 0.4 | 9 ± 0.4 | 9 ± 0.4 |
| (+)-Norpseudoephedrine | U | 6 ± 0.2 | 6 ± 0.2 | 9 ± 0.2 | 9 ± 0.2 | 9 ± 0.2 | 9 ± 0.2 |
| | T | 6 ± 0.2 | 6 ± 0.2 | 9 ± 0.2 | 9 ± 0.2 | 9 ± 0.2 | 9 ± 0.2 |
| Metaraminol Bitartrate | U | 5 ± 0.2 | 5 ± 0.2 | 10 ± 0.2 | 10 ± 0.2 | 10 ± 0.2 | 10 ± 0.2 |
| Salt, USP | T | 5 ± 0.2 | 5 ± 0.2 | 10 ± 0.2 | 10 ± 0.2 | 10 ± 0.2 | 10 ± 0.2 |
| Mephentermine | U | 6 ± 0.4 | 6 ± 0.4 | 6 ± 0.3 | 6 ± 0.3 | 6 ± 0.3 | 6 ± 0.3 |
| Hemisulfate Salt | T | 6 ± 0.3 | 6 ± 0.3 | 7 ± 0.7 | 8 ± 0.7 | 6 ± 0.4 | 6 ± 0.4 |

Results are as mean ± S.E. of five-six rabbits per drug.
U = Untreated contralateral eye
T = Drug treated eye

TABLE 10

Mydriatic Responses

| DRUGS | TREATED EYE | | UNTREATED EYE | |
|---|---|---|---|---|
| SALINE | | 0 | | 0 |
| (+)-Pseudoephedrine | 1% | + | 1% | 0 |
| | 2% | + | 2% | 0 |
| (−)-Pseudoephedrine | 1% | + | 1% | 0 |
| | 2% | + | 2% | 0 |
| (+)-Ephedrine | 1% | ++ | 1% | 0 |
| | 2% | ++ | 2% | 0 |
| (−)-Ephedrine | 1% | 0 | 1% | 0 |
| | 2% | +++ | 2% | +++ |
| (−)-Phenylpropanolamine | 1% | ++ | 1% | + |
| | 2% | ++ | 2% | 0 |
| (+)-Phenylpropanolamine | 1% | + | 1% | 0 |
| | 2% | ++ | 2% | + |
| (−)-Phenylephrine | 1% | ++ | 1% | 0 |
| | 2% | +++ | 2% | +++ |
| (+)-Phenylephrine | 1% | +++ | 1% | +++ |
| | 2% | +++ | 2% | +++ |
| (−)-Norpseudoephedrine | 1% | + | 1% | + |
| | 2% | ++ | 2% | ++ |
| (+)-Norpseudoephedrine | 1% | ++ | 1% | + |
| | 2% | ++ | 2% | ++ |
| Metaraminol Bitartrate | 1% | ++ | 1% | 0 |
| Salt, USP | 2% | +++ | 2% | +++ |
| Mephentermine Hemisulfate | 1% | ++ | 1% | 0 |
| Salt | 2% | + | 2% | 0 |

SCALE:
0 = No change;
+ = 0–2 mm change;
++ = 2–4 mm change;
++ = >4 mm change.

EXAMPLE 4

Central Nervous System Stimulation and Depression

Many sympathomimetic compounds stimulate the central nervous system, which is one reason that decongestants frequently have such side effects as insomnia. These tests compare the degree of central nervous system stimulation and depression for the present diastereomers with known sympathomimetics like (+)-pseudoephedrine, (−)-ephedrine and (−)-phenylephrine.

Moreover, decongestants are often sold in combination with other active ingredients (e.g. Claritin-D® and Seldane-D®). In products containing two or more active ingredients, interactions between the active ingredients are undesirable. In these tests, the extent of interaction of the present diastereomers with a known antihistamine, tripolidine, was also observed.

Methods:

Animals

Male Swiss-Webster mice (HSD ND4, Harlan Sprague Dawley, Houston, Tex.) aged 2–3 months were used in these studies. Each dose group consisted of 8 mice. The mice were housed 2 to 4 per cage in 30.4×22.9×15.2 cm clear polycarbonate cages with food and water available ad libitum for at least one week prior to locomotor activity testing. The colony was maintained at 23±1° C., on a normal light-dark cycle beginning at 0700 hr. All testing took place during the light portion of the light-dark cycle.

Apparatus

Horizontal (forward movement) locomotor activity was measured using a standardized, optical activity monitoring system [Model KXYZCM (16), Omnitech Electronics, Columbus, Ohio]. Activity was monitored in forty 40.5× 40.5×30.5 cm clear acrylic chambers that where housed in sets of two within larger sound-attenuating chambers. A panel of 16 infrared beams and corresponding photodetectors were spaced 2 cm apart along the sides and 2.4 cm above the floor of each activity chamber. A 7.5-W incandescent light above each chamber provided dim illumination via a rheostat set to 20% of full scale. Fans provided an 80-dB ambient noise level within the chamber.

Drugs.

(+)-Amphetamine, (−)-ephedrine, (+)-ephedrine, (−)-pseudoephedrine, (+)-pseudoephedrine, (−)-phenylpropanolamine, (+)-phenylpropanolamine, (−)-phenylephrine, (+)-phenylephrine, and mephentermine were obtained from Sigma Chemical Co. (+)-Norpseudoephedrine, (−)-norpseudoephedrine, and R-(R*,S*) metaraminol were obtained from Chemsyn Laboratories (Lenexa, Kans.). Triprolidine HCl was obtained from Research Biochemicals International, (Natick, Mass.). All compounds were dissolved in 0.9% saline and injected i.p. in a volume of 10 ml/kg body weight, except for (−)-pseudoephedrine, which was dissolved in 0.16% tartaric acid in deionized water.

Procedure.

Locomotor stimulant effects. In these studies, mice were placed in the activity testing chambers immediately following injection of saline or a dose of one of the test compounds ranging from 0.1 mg/kg to 250 mg/kg. (+)-Amphetamine was used as a positive control. The total horizontal distance traversed (cm) was recorded at 10 minute intervals for a 2-hour session. Separate groups of 8 mice were assigned to each dose or saline group, and dose-effect testing continued for each compound until maximal stimulant or depressant effects could be estimated. A separate control group was tested along with each compound.

For compounds with significant stimulant effects, the potency and efficacy were estimated for the 30-minute time period in which maximal stimulant effects were observed at the lowest dose. Using TableCurve 2D v2.03 (Jandel Scientific), the mean average total distance traversed (cm/10 min) for that period was fit to a 3-parameter logistic peak function of $\log_{10}$ dose (with the constant set to the mean of the saline group), and the maximum effect estimated from the resulting curve. The $ID_{50}$ (dose producing ½ maximal stimulant activity) was estimated from a linear regression against $\log_{10}$ dose of the ascending portion of the dose-effect curve. The stimulant efficacy was the peak effect of the compound (cm/10 min) as estimated from the logistic peak function, minus the mean control distance traveled (cm/10 min), and was expressed for each stimulant compound as a ratio to the stimulant efficacy determined for (+)-amphetamine.

For compounds with significant depressant effects, the potency and efficacy were estimated for the 30-minute time period in which maximal depression occurred at the lowest dose. The mean average total distance traversed (cm/10 min) for that period were fit to a linear function of $\log_{10}$ dose of the descending portion of the dose-effect curve. The $ID_{50}$ was the dose producing ½ maximal depressant activity, where maximal depression=0 cm/30 min. Efficacy was the ratio of maximal depressant effect to maximum possible depression for each compound (mean average total distance of the control group minus the lowest mean total distance, expressed as a ratio to the control group total distance).

$H_1$ receptor antagonist interaction studies. The potential for each compound to interact with $H_1$ antihistamines was determined by testing whether a known antihistamine produced a dosage shift in the observed stimulant or depressant effects of each sympathomimetic compound. Triprolidine was used as an example of the class of $H_1$ receptor antagonists that are typically used as antihistaminic drugs. Twenty minutes prior to administering each test compound, either triprolidine (at 0.01, 0.1, 1.0, or 25 mg/kg) or saline was injected. The mice were immediately placed in the activity testing chamber for a 2-h session. Doses of the test compound were selected from the ascending or descending time of the dose-effect curve determined from the compound-alone studies. Eight mice were tested for each triprolidine/test compound combination.

Statistical analysis. Time course data for each compound were considered in 2-way analyses of variance with dose as a between-group and time as a within-group factor. The dose-effect data were considered in 1-way analyses of variance, and planned individual comparisons were conducted between each dose and the saline control group. Interaction studies were considered in 2-way analyses of variance, with Pretreatment and Test dose as the factors.

Two-way analyses of variance were conducted on horizontal distance traveled using dose as a between-subject factor and time as a within-subject factor. Only (+)-amphetamine exhibited a significant dose- and time-effect, with an interaction of dose and time (all Fs>2.7; all p values <0.01).

Results:

The effects of the stereoisomers on locomotor activity are summarized in Table 11.

Locomotor Stimulant Effects

Time Course.

Mice injected with (+)-amphetamine showed a dose- and time-dependent increase in the distance traversed within 10 minutes following injection. The peak stimulant effects occurred during the first 30 minutes following 2.5 mg/kg and continued for at least 60 minutes.

Dose-dependent increases in locomotor activity of slower onset and longer duration were evident for (−)-ephedrine, (−)-norpseudoephedrine, and (+)-norpseudoephedrine. (−)-Ephedrine resulted in increased locomotion within 40 minutes following a dosage of 50 to 100 mg/kg, with peak effects occurring 60–90 minutes following injection and diminishing thereafter.

A small increase in locomotor activity was evident following 100 mg/kg (+)-ephedrine, although most doses of this compound were without effect or depressed locomotor activity. Both (+) and (−)-norpseudoephedrine resulted in dose and time-dependent locomotor activity increases. However, those following (+)-norpseudoephedrine treatment had a higher maximal magnitude and occurred more rapidly following injection. Irrespective of magnitude, the effects of norpseudoephedrine appeared to be of longer duration when compared with (−)-ephedrine.

Mephentermine resulted in increased locomotion following from 5 to 25 mg/kg, with effects occurring within 20 minutes and lasting for up to 80 minutes. The peak effects of mephentermine incurred 20–50 minutes following rejection.

Two-way analyses of variance were conducted on horizontal distance traveled using dose as a between-subject factor and time as a within-subject factor. Each of the following compounds exhibited a significant dose- and time-effect, with an interaction of dose and time (all Fs>2.7; all p values <0.01): (+)-amphetamine, (−)-ephedrine, (+)-ephedrine, (−)-norpseudoephedrine, (+)-norpseudoephedrine and mephentermine.

Locomotor Depressant Effects

Time Course.

With the exceptions of (+)-amphetamine, (−)-ephedrine, norpseudoephedrine, and mephentermine, all of the sympathomimetics resulted in locomotor depression. Seven compounds exhibited a dose-dependent locomotor depression within 10 to 20 minutes following injection: (+)-pseudoephedrine, (−)-pseudoephedrine, (+)-ephedrine, (−)-phenylpropanolamine, (−)-phenylephrine, (+)-phenylephrine, and R-(R*,S*)metaraminol. These effects lasted from 20 minutes to >2 hours, depending upon dose and compound. (+)-Phenylpropanolamine resulted in locomotor depression which was not evident until 90 minutes following injection. One of the compounds, (−)-norpseudoephedrine, gave rise to locomotor stimulation within 40 minutes following injection, but exhibited locomotor depression at an earlier time (10–40 minutes following injection) and with a lower dose range. Two-way analyses of variance conducted on horizontal distance traveled for the compounds resulting in depression confirmed the observations of time- and dose-dependent effects, with each analysis indicating a significant interaction of dose and time (all Fs>1.7-all p values <0.001).

Depressant Efficacy/Potency.

Dose-response relationships for locomotor depressant effects of the sympathomimetics are provided in Table 11, for the time period in which the maximal depressant effects were first observed as a function of dose. The maximal depressant effect was estimated as the difference between the control group mean and the mean of the dose group with lowest locomotor activity. The maximum possible effect was assumed to be equivalent to the mean of the control group. Depressant efficacy was the ratio of maximal depressant effect to the maximum possible effect, and was highest for (+)-pseudoephedrine (0.58). The $ID_{50}$ for depressant effects was estimated from a linear regression through the descending portion of the dose-effect curve, assuming zero locomotor activity (horizontal distance) as the maximal effect. The order of potency for the depression was:

(−)-phenylephrine=(+)-phenylpropanolamine>(+)-ephedrine=(−)-norpseudoephedrine=(−)-phenylpropanolamine=R-(R*,S*)metaraminol>(−)-pseudoephedrine>(+)-phenylephrine>(+)-pseudoephedrine.

TABLE 11

| Compound | Range[1] | Stimulation[8] | | | Depression | | |
|---|---|---|---|---|---|---|---|
| | | Efficacy[2] | Potency[3] | Time[4] | Efficacy[5] | Potency[6] | Time[7] |
| (+)-Pseudoephedrine | 1–100 | 0.21 | 12.6 | 40–70 | 0.58 | 72.4 | 10–40 |
| (−)-Pseudoephedrine | 5–100 | 0.21 | 14.6 | 80–110 | 0.84 | 38.5 | 10–40 |
| (+)-Ephedrine | 1–250 | 0.25 | 84.9 | 50–80 | 0.85 | 4.4 | 10–40 |
| (−)-Ephedrine | 0.5–250 | 0.80 | 38.2 | 50–80 | 0.45 | ≈7.4 | 10–40 |
| (+)-Phenylpropanolamine | 2.5–25 | 0.19 | 7.9 | 50–80 | 0.76 | 2.6 | 90–120 |
| (−)-Phenylpropanolamine | 1–25 | 0 | — | 60–90 | 0.70 | 5.8 | 10–40 |
| (−)-Phenylephrine | 0.1–10 | 0 | — | 60–90 | 0.77 | 2.3 | 0–30 |
| (+)-Phenylephrine | 5–100 | 0 | — | 60–90 | 0.65 | 53.3 | 0–30 |
| (+)-Norpseudoephedrine | 5–50 | 1.23 | 12.2 | 30–60 | 0.26 | — | 10–40 |
| (−)-Norpseudoephedrine | 2.5–250 | 0.62 | 51.1 | 40–70 | 0.68 | 3.9 | 10–40 |
| R-(R*,S*) metaraminol | 0.25–10 | 0 | — | 90–120 | 0.87 | 4.3 | 30–60 |
| mephentermine | 0.5–25 | 1.25 | 5.6 | 20–50 | 0 | — | 0–30 |

[1]Dose range tested in mg/kg.
[2]The ratio of the maximal stimulant effect of the test compound to the maximal effect of (+)-amphetamine.
[3]The dose resulting in ½ the maximal stimulant effect ($ID_{50}$) in mg/kg i.p.
[4]The 30-min period following injection in which the maximal stimulant effect occurred.
[5]The ratio of the maximal depressant effect to the maximum possible effect (zero locomotor activity).
[6]The dose resulting in ½ the maximal depressant effect ($ID_{50}$) in mg/kg i.p.
[7]The 30-min minute period following injection in which the maximal depression occurred.
[8]"—" denotes absence of significant effect Triprolidine Interactions.

Triprolidine alone. When injected immediately prior to testing, doses of triprolidine from 0.25 to 25 mg/kg failed to affect horizontal distance during the 2-hour test period. Dose-dependent depression of locomotion was observed following 50 and 100 mg/kg, beginning within 10-minutes following injection and lasting for 30 to 40 minutes. A separate one-way analysis of variance on average distance/ 10 min for the period 0–30 minutes following injection suggested a significant dose main effect where F(8,102)=7.7 and p<0.001, although individual comparisons of dose groups with control in that analysis verified that significant effects of triprolidine were restricted to the 50 and 100 mg/kg doses (ps<0.01).

Triprolidine Interactions.

Significant effects for pretreatment with triprolidine were only observed for the depressant compounds (+)-pseudoephedrine and (+)-phenylpropanolamine, and the stimulant compounds (−)-ephedrine, and (−)-norpseudoephedrine.

When tested for dose-response in mice pretreated with 0.01, 0.1, or 1.0 mg/kg triprolidine, the compounds (−)-pseudoephedrine, (+)-ephedrine, (−)-phenylpropanolamine, (+)-norpseudoephedrine, (−)-phenylephrine, (+)-phenylephrine, R-(R*,S*)metaraminol, and mephentermine failed to show significant modification of stimulant or depressant effects.

EXAMPLE 5

Decongestant Activity

The decongestant activity of the present diastereomers was compared in normal and histamine-challenged rats to that of a known decongestant, (t)-pseudoephedrine.

Experimental Protocol:

The method was based on one reported by Lung for the measurement of nasal airway resistance. Sprague Dawley rats (weight range 247–365 gram) were anesthetized with sodium pentobarbital intra-peritoneally (50 mg/ka). Rats were placed on a heating pad, in a V trough, dorsal side down. A tracheotomy was performed and a tracheal cannula was positioned, tied and left open to room air. A cannula was placed into the superior part of the trachea and was advanced until it lodged in the posterior nasal opening. Normal saline (0.5 ml) was injected into the nasal cannula to confirm position as well as to moisten the nasal mucosa. After nasal cannulation was confirmed the cannula was tied in place with a suture placed around the trachea Excess fluid was expelled from the nasal airway with a short (2–3 second) air flow via the nasal cannula. Additionally, in studies correlating blood pressure changes to those in the nasal airway pressure, a cannula was positioned in the internal carotid artery (PE. 50) and connected to a multipen (Grass) recorder using pressure transducer (Isotec).

Nasal airway pressure was measured using a validyne pressure transducer (with a 2.25 cm $H_2O$ range membrane) connected to a multipen recorder (Grass). Air was passed through an in-line direct measure flow meter (Gilmont instruments) connected to the nasal opening cannula. Pressure was measured in the line with a constant flow rate (150 ml/min) of air. Drugs were directly injected into the jugular vein using a 30 gauge needle. All injections were of a constant 0.1 ml volume. In the congestion challenged groups congestion was achieved by an intranasal administration of histamine (50 mM, 0.02 ml/nostril). The histamine was expelled after 2 min with a short nasal cannula airflow and subsequent drug doses were directly injected into the jugular vein. The doses of injection for each of the enantiomers tested were determined from a previous study in our laboratory in which each of the dose of drug we chose resulted in an increase in mean arterial pressure (MAP) of 10% (Table 13). The dose causing a 10% increase in MAP served as our "100%" dose for the initial nasal airway studies.

TABLE 13

Dosage of Enantiomer which raised mean arterial pressure 10%

| Drug Name | Dog (ug/kg) | Rat (ug) |
| --- | --- | --- |
| (+)-pseudoephedrine | 200 | 60 |
| (−)-pseudoephedrine | 1400 | 420 |
| (+)-ephedrine | 200 | 60 |
| (−)-ephedrine | 100 | 30 |
| (−)-phenylpropanolamine | 20 | 6 |
| (+)-phenylpropanolamine | 400 | 120 |
| (−)-phenylephrine | 10 | 3–5 |
| (+)-phenylephrine | 80 | 24 |

Two Investigations were Performed as Follows:

Investigation 1: A comparison was made of the effect of the different enantiomers on nasal airway resistance prior to and following histamine-induced congestion. The amount of drug required to raise the mean arterial pressure by 10% was chosen as the "100% dose" for these decongestant studies. See Table 13. Control changes in nasal airway resistance were obtained by recording nasal airway resistance prior to and following this 100% dose. In a test group of rats the 100% dose was injected into the jugular vein two minutes after nasal airway congestion was produced by introduction of 0.02 ml/nostril of 50 mM histamine into the nasal airway. Nasal airway resistance was thus increased after the histamine challenge and the effect of administering an enantiomer on this histamine-induced airway resistance was observed.

Investigation 2: A comparison of the effect of enantiomer dosage on nasal airway resistance was made to determine an effective dosage range of each enantiomer. Dosages tested were 50%, 25%, 10% and 5% of the "100%" enantiomer dosage required to increase the mean arterial pressure 10%. Changes in nasal airway resistance were obtained by comparing pre-enantiomer injection nasal airway resistance with decreases in nasal airway resistance following jugular vein injection of the enantiomer dosage. Five rats were tested at each dose for each of the enantiomers.

Investigation 3: A 75% dose of enantiomer was tested following 0.02 ml/nostril of 50 mM histamine. As before, this "75% dose" was 75% of the dose required to increase the mean arterial pressure 10%. The 75% dosages employed were as provided in Table 14.

TABLE 14

| Drug | 75% Dosage (µg/kg i.v.) |
| --- | --- |
| (+)-pseudoephedrine | 150 |
| (+)-ephedrine | 150 |
| (−)-ephedrine | 75 |
| (−)-phenylpropanolamine | 15 |
| (+)-phenylpropanolamine | 300 |
| (−)-phenylephrine | 7.5 |
| (+)-phenylephrine | 60 |

Blood pressure was monitored. Effects on airway resistance and blood pressure of each of the eight stereoisomers were evaluated at the 75% dose prior to and following histamine in five rats for each enantiomer and each histamine condition.

Results

Investigation 1:

Each drug gave rise to a significant decrease in nasal airway pressure, relative to control, in non-histamine-challenged rats (Table 15). While the control for the (−)-phenylephrine was significantly different from the other controls, this difference in control level did not translate into a difference caused by administration of the drug.

TABLE 15

| Drug | Control (mm $H_2O$) | Post Drug (mm $H_2O$) | % Change | Paired t test pValue |
| --- | --- | --- | --- | --- |
| (+)-pseudoephedrine | 9 ± 0.5 | 7 ± 0.9 | −21.3 ± 7.6 | 0.015 |
| (−)-pseudoephedrine | 9 ± 0.1 | 8 ± 0.2 | −12.0 ± 2.4 | 0.008 |
| (+)-ephedrine | 8 ± 0.6 | 7 ± 0.9 | −21.4 ± 5.4 | 0.008 |
| (−)-ephedrine | 7 ± 0.8 | 6 ± 0.5 | −14 ± 3.4 | 0.034 |

TABLE 15-continued

| Drug | Control (mm H₂O) | Post Drug (mm H₂O) | % Change | Paired t test pValue |
|---|---|---|---|---|
| (+)-phenylpropanolamine | 7 ± 0.2 | 6 ± 0.2 | −10.5 ± 1.4 | 0.001 |
| (−)-phenylpropanolamine | 8 ± 0.6 | 7 ± 0.7 | −8.81 ± 2.6 | 0.028 |
| (−)-phenylephrine | 5 ± 0.2 | 4 ± 0.2 | −20.3 ± 4.3 | 0.010 |
| (+)-phenylephrine | 9 ± 0.4 | 8 ± 0.3 | −12.2 ± 3.1 | 0.024 |

*mm water.

In the histamine-challenged rats, administration of each drug again showed a significant decrease in nasal passage pressure (Table 16, FIG. 1).

TABLE 16

| Drug | Control* | t test p Value | Post* Histamine | t test p Value | Post* Drug | % Change |
|---|---|---|---|---|---|---|
| (+)-pseudo-ephedrine | 6.6 ± 0.6 | 0.1 | 9.3 ± 1.8 | 0.001 | 6.1 ± 1.5 | −36.7 ± 2.7 |
| (−)-pseudo-ephedrine | 9.5 ± 1.9 | 0.4 | 10.5 ± 1.3 | 0.003 | 7.9 ± 1.1 | −24.7 ± 3.4 |
| (+)-ephedrine | 8.0 ± 0.6 | 0.01 | 10.2 ± 0.5 | 0.002 | 8.2 ± 0.3 | −19.4 ± 2.1 |
| (−)-ephedrine | 6.7 ± 0.4 | 0.06 | 8.2 ± 0.7 | 0.007 | 6.4 ± 0.6 | −21.8 ± 3.5 |
| (+)-phenyl-propanolamine | 0.5 ± 0.9 | 0.004 | 12.2 ± 0.8 | 0.04 | 10.6 ± 1.0 | −13.6 ± 4.4 |
| (−)-phenyl-propanolamine | 7.8 ± 0.2 | 0.07 | 10.5 ± 1.0 | 0.04 | 7.6 ± 0.4 | −25.2 ± 5.6 |
| (−)-phenyl-ephrine | 7.5 ± 0.5 | 0.04 | 13.2 ± 2.1 | 0.05 | 10.5 ± 2.1 | −22.3 ± 8.5 |
| (+)-phenyl-ephrine | 6.5 ± 0.4 | 0.07 | 8.7 ± 1.1 | 0.007 | 5.5 ± 0.5 | −35.2 ± 2.5 |

*mm water.

Investigation #2:

Table 17 summarizes the mean nasal airway pressure of different enantiomer dosages ranging from 5%, 10%, 25% and 50% of the dose that produced a 10% change in resting mean arterial pressure (the "100%" dose). The standard error of the mean is also provided. In general, the 50% dose was an approximate threshold dose at which nasal airway pressure was reduced.

TABLE 17

Mean Decrease in Nasal Airway Pressure With Variable Enantiomer Dosages*

| Drug # | 5% | 10% | 25% | 50% |
|---|---|---|---|---|
| (+)-pseudoephedrine | −3.8 ± 2.8 | −6.8 ± 3.6 | −13.5 ± 4.3 | −16.1 ± 2.4 |
| (−)-pseudoephedrine |  | −0.03 ± 0.8 | −0.5 ± 0.6 | −1.9 ± 4.4 |
| (+)-ephedrine | −2.6 ± 1.0 | 3.0 ± 1.0 | −0.1 ± 1.4 | −1.0 ± 3.3 |
| (−)-ephedrine | −1.0 ± 0.8 | −2.5 ± 1.5 | −3.6 ± 1.9 | −1.9 ± 2.0 |
| (+)-phenylpropanol-amine | −0.03 ± 0.3 | −0.7 ± 1.2 | −0.8 ± 1.0 | −0.07 ± 1.5 |
| (−)-phenylpropanol-amine | 0.1 ± 0.7 | −1.4 ± 0.5 | −1.4 ± 2.1 | −1.9 ± 0.6 |
| (−)-phenylephrine | −1.6 ± 0.9 | −4.8 ± 0.8 | −12.1 ± 2.3 | −5.2 ± 1.6 |
| (+)-phenylephrine | −4.00 ± 1.2 | −2.5 ± 1.0 | −4.6 ± 1.4 | −10.2 ± 3.9 |

*percent enantiomer dose that increased the dog resting mean arterial pressure 10%.

Investigation #3:

FIG. 2 summarizes the percent change in mean arterial blood pressure after a 75% dose of various enantiomers.

FIG. 3 provides the observed percent nasal airway pressure after a 75% dose of the different enantiomers.

What is claimed is:

1. A stereoscopically-pure diastereomer of Formula I:

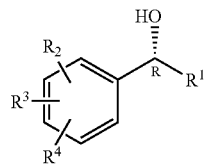

wherein:

$R^1$ is pyridine which may be substituted with hydrogen, lower alkyl, lower alkylenearyl, lower alkylenephenyl, lower alkylenehydroxyphenyl, lower alkyleneamine, lower alkyleneaminoaryl, or lower alkylaminohydroxyphenyl;

$R^2$, $R^3$ and $R^4$ are independently H, OH, CH₂OH, NHCONH₂, or NH₂; wherein $R^2$, $R^3$ and $R^4$ are not all H; and with the proviso that the stereoisomer is not (−)-phenylpropanolamine, (−)-phenylephrine or (−)-ephedrine.

* * * * *